United States Patent
Ben-Haim

(10) Patent No.: US 10,646,183 B2
(45) Date of Patent: May 12, 2020

(54) DETECTION OF SCAR AND FIBROUS CARDIAC ZONES

(71) Applicant: Tylerton International Inc., Road Town (VG)

(72) Inventor: Shlomo Ben-Haim, London (GB)

(73) Assignee: Tylerton International Inc., Road Town (VG)

( * ) Notice: Subject to any disclaimer, the term of this patent is extended or adjusted under 35 U.S.C. 154(b) by 730 days.

(21) Appl. No.: 15/110,756

(22) PCT Filed: Jan. 8, 2015

(86) PCT No.: PCT/IB2015/050148
§ 371 (c)(1),
(2) Date: Jul. 11, 2016

(87) PCT Pub. No.: WO2015/104672
PCT Pub. Date: Jul. 16, 2015

(65) Prior Publication Data
US 2016/0331337 A1   Nov. 17, 2016

Related U.S. Application Data

(63) Continuation-in-part of application No. PCT/IL2014/050089, filed on Jan. 24, 2014, and a (Continued)

(51) Int. Cl.
*A61B 34/20* (2016.01)
*A61B 6/00* (2006.01)
(Continued)

(52) U.S. Cl.
CPC .......... *A61B 6/503* (2013.01); *A61B 6/037* (2013.01); *A61B 6/465* (2013.01); *A61B 6/466* (2013.01);
(Continued)

(58) Field of Classification Search
CPC ........................................ A61B 6/503
See application file for complete search history.

(56) References Cited

U.S. PATENT DOCUMENTS 5,077,035 A   12/1991   Wieland et al.
5,789,420 A    8/1998   Efange et al.
(Continued)

FOREIGN PATENT DOCUMENTS

CN   1981710     6/2007
CN   101005874   7/2007
(Continued)

OTHER PUBLICATIONS

Notice of Reason for Rejection dated May 9, 2017 From the Japan Patent Office Re. Application No. 2015-554307 and Its Translation Into English. (16 Pages).
(Continued)

*Primary Examiner* — Omkar A Deodhar

(57) ABSTRACT

A method of tissue recognition of tissue type in a heart or other tissue, comprising:
(i) injecting a patient with a radioactive tracer;
(ii) collecting radiation emitted from cardiac tissue
(iii) associating said collected radiation with a wall of the heart; and
(iv) analyzing said associated radiation to recognize fibrous tissue in the heart wall. Optionally, the resolution of the association is better than 5 mm.

31 Claims, 20 Drawing Sheets

Related U.S. Application Data continuation-in-part of application No. PCT/IL2014/050090, filed on Jan. 24, 2014, and a continuation-in-part of application No. PCT/IB2014/064316, filed on Sep. 8, 2014, and a continuation-in-part of application No. PCT/IB2014/064319, filed on Sep. 8, 2014.

(60) Provisional application No. 61/925,669, filed on Jan. 10, 2014, provisional application No. 62/030,740, filed on Jul. 30, 2014, provisional application No. 62/030,917, filed on Jul. 30, 2014, provisional application No. 61/925,670, filed on Jan. 10, 2014, provisional application No. 62/003,108, filed on May 27, 2014.

(51) Int. Cl.
*A61B 6/03* (2006.01)
*G06T 7/00* (2017.01)

(52) U.S. Cl.
CPC .......... *A61B 6/486* (2013.01); *A61B 6/5211* (2013.01); *A61B 6/5217* (2013.01); *G06T 7/0012* (2013.01); *G06T 2207/10076* (2013.01); *G06T 2207/10104* (2013.01); *G06T 2207/10108* (2013.01); *G06T 2207/30048* (2013.01)

(56) References Cited

U.S. PATENT DOCUMENTS

| | | | |
|---|---|---|---|
| 6,211,360 | B1 | 4/2001 | Glick et al. |
| 6,358,492 | B1 | 3/2002 | Kuhar et al. |
| 6,490,480 | B1 | 12/2002 | Lerner |
| 6,511,500 | B1 | 1/2003 | Rahme |
| 6,845,267 | B2 | 1/2005 | Harrison et al. |
| 7,363,076 | B2 | 4/2008 | Yun et al. |
| 7,729,752 | B2 * | 6/2010 | Harlev ............ A61B 5/0422 600/509 |
| 8,359,092 | B2 | 1/2013 | Hayam et al. |
| 8,364,285 | B2 | 1/2013 | Rezai |
| 8,440,168 | B2 | 5/2013 | Yang et al. |
| 2004/0138550 | A1 | 7/2004 | Hartlep et al. |
| 2005/0004465 | A1 | 1/2005 | Abuhamad |
| 2005/0008126 | A1 | 1/2005 | Juh et al. |
| 2005/0080327 | A1 | 4/2005 | Jenkins et al. |
| 2005/0215889 | A1 | 9/2005 | Patterson, II |
| 2005/0261672 | A1 | 11/2005 | Deem et al. |
| 2006/0085049 | A1 | 4/2006 | Cory et al. |
| 2006/0127309 | A1 | 6/2006 | Raffel et al. |
| 2006/0287648 | A1 | 12/2006 | Schwartz |
| 2007/0016028 | A1 | 1/2007 | Donaldson et al. |
| 2007/0049817 | A1 | 3/2007 | Preiss et al. |
| 2007/0106337 | A1 | 5/2007 | Errico et al. |
| 2007/0127793 | A1 | 6/2007 | Beckett et al. |
| 2008/0146914 | A1 | 6/2008 | Polzin et al. |
| 2008/0161803 | A1 | 7/2008 | Oral et al. |
| 2008/0279436 | A1 | 11/2008 | Razifar et al. |
| 2009/0192393 | A1 | 7/2009 | Hayam et al. |
| 2009/0192394 | A1 | 7/2009 | Guttag et al. |
| 2010/0193696 | A1 | 8/2010 | Blevis et al. |
| 2010/0221182 | A1 | 9/2010 | Purohit et al. |
| 2010/0268289 | A1 | 10/2010 | Chen et al. |
| 2010/0312128 | A1 | 12/2010 | Karst et al. |
| 2011/0087088 | A1 | 4/2011 | Korn et al. |
| 2011/0144723 | A1 | 6/2011 | Streeter et al. |
| 2011/0152974 | A1 | 6/2011 | Rezai et al. |
| 2011/0189096 | A1 | 8/2011 | Watanabe et al. |
| 2011/0218818 | A1 | 9/2011 | Butson et al. |
| 2011/0230775 | A1 | 9/2011 | Barley et al. |
| 2011/0238128 | A1 | 9/2011 | Dobak, III |
| 2011/0306846 | A1 | 12/2011 | Osorio |
| 2012/0065492 | A1 | 3/2012 | Gertner et al. |
| 2012/0155733 | A1 | 6/2012 | Wagenknecht |
| 2012/0271171 | A1 | 10/2012 | Gertner |
| 2013/0072790 | A1 | 3/2013 | Ludwig et al. |
| 2013/0116681 | A1 | 5/2013 | Zhang |
| 2013/0123773 | A1 | 5/2013 | Schwartz |
| 2013/0131746 | A1 | 5/2013 | Simon et al. |
| 2015/0327805 | A1 | 11/2015 | Ben-Haim |
| 2015/0351834 | A1 | 12/2015 | Ben-Haim et al. |
| 2015/0359430 | A1 | 12/2015 | Ben-Haim |
| 2015/0366523 | A1 | 12/2015 | Ben-Haim |
| 2016/0027342 | A1 | 1/2016 | Ben Haim |
| 2016/0217571 | A1 | 7/2016 | Ben-Haim |
| 2016/0220835 | A1 | 8/2016 | Ben-Haim |

FOREIGN PATENT DOCUMENTS

| | | |
|---|---|---|
| CN | 101137326 | 3/2008 |
| CN | 101219058 | 7/2008 |
| CN | 101687780 | 3/2010 |
| CN | 101859641 | 10/2010 |
| CN | 102120039 | 7/2011 |
| CN | 102223838 | 10/2011 |
| CN | 102740769 | 10/2012 |
| EP | 1733692 | 12/2006 |
| EP | 2474526 | 7/2012 |
| EP | 2591722 | 5/2013 |
| JP | 2007-144175 | 6/2007 |
| JP | 2008-149147 | 7/2008 |
| JP | 2008-259696 | 10/2008 |
| JP | 2010-514786 | 5/2010 |
| JP | 2010-178949 | 8/2010 |
| JP | 2012-509701 | 4/2012 |
| JP | 2013-103134 | 5/2013 |
| KR | 20090074399 | 7/2009 |
| WO | WO 01/82978 | 11/2001 |
| WO | WO 02/102238 | 12/2002 |
| WO | WO 2005/053615 | 6/2005 |
| WO | WO 2007/002541 | 1/2007 |
| WO | WO 2008/009021 | 1/2008 |
| WO | WO 2008/083056 | 7/2008 |
| WO | WO 2008/121578 | 10/2008 |
| WO | WO 2009/022271 | 2/2009 |
| WO | WO 2010/058372 | 5/2010 |
| WO | WO 2011/046879 | 4/2011 |
| WO | WO 2011/091069 | 7/2011 |
| WO | WO 2011/110959 | 9/2011 |
| WO | WO 2012/011036 | 1/2012 |
| WO | WO 2012/061153 | 5/2012 |
| WO | WO 2013/036869 | 3/2013 |
| WO | WO 2014/115148 | 7/2014 |
| WO | WO 2014/115150 | 7/2014 |
| WO | WO 2014/115151 | 7/2014 |
| WO | WO 2014/115152 | 7/2014 |
| WO | WO 2014/141247 | 9/2014 |
| WO | WO 2015/033317 | 3/2015 |
| WO | WO 2015/033319 | 3/2015 |
| WO | WO 2015/104672 | 7/2015 |
| WO | WO 2015/181753 | 12/2015 |

OTHER PUBLICATIONS

Katafuchi "Cardiac Radionuclide Imaging", Japanese Journal of Radiological Technology, 64(5): 626-637, 2008. & English Abstract.
Klein et al. "Abstract 17871: Assessment of Global Cardiac Innervation Using 1123-Meta-Iodobenzylguanidine Before and After Ventricular Tachycardia Ablation", Circulation, 126(Suppl.21): # 17871, Nov. 20, 2012.
Shoda "Catheter Ablation for Atrial Fibrillation in Patients With Heart Failure", Japanese Journal of Electrocardiology, 31(2): 205-207, 2011.
Sumiyoshi "New Diagnostic Methods and Non Pharmacological Therapies in Cardiac Arrhythmias", Juntendo Medical Journal, 42(4): 450-458, 1997.
Official Action dated Jun. 26, 2017 From the U.S. Patent and Trademark Office Re. U.S. Appl. No. 14/917,285. (35 pages).
Unknown "SPECT CT Fusion Image", Imaging Diagnosis in Nuclear Medicine, 24(1): 52-59, 2009. Partial English Translation.

(56) References Cited

OTHER PUBLICATIONS

Official Action dated Aug. 10, 2017 From the U.S. Patent and Trademark Office Re. U.S. Appl. No. 14/762,933. (47 pages).
Notification of Office Action and Search Report dated Dec. 2, 2016 From the State Intellectual Property Office of the People's Republic of China Re. Application No. 201480005617.0 and Its Summary in English.
Supplementary European Search Report and the European Search Opinion dated Feb. 9, 2016 From the European Patent Office Re. Application No. 14743909.5. (9 Pages).
Abi-Jaoudeh et al. "Multimocality Image Fusion-Guided Procedures: Technique, Accuracy, and Applications", Cardiovascular and Interventional Radiology, 35(5): 986-998, Published Online Aug. 1, 2012.
Bercier et al. "Multimodality Image Fusion for Radiosurgery Localisation of Large AVMs", Proceedings of the 22nd Annual International Conference of the IEEE Engineering in Medicine and Biology Society, EMBS, Chicago, IL, USA, Jul. 23-29, 2000, XP002422677, 4: 2689-2692, Jul. 23, 2000.
Gering et al. "An Integrated Visualization System for Surgical Planning and Guidance Using Image Fusion and an Open MR", Journal of Magnetic Resonance Imaging, XP002239881, 13(6): 967-975, Jun. 2001.
Levin et al. "Techniques for Efficient, Real-Time, 3D Visualization of Multi-Modality Cardiac Data Using Consumer Graphics Hardware", Computerized Medical Imaging and Graphics, 29(6): 463-475, Sep. 30, 2005.
Mallouhi et al. "3 T MR Tomography of the Brachial Plexus: Structural and Microstructural Evaluation", European Journal of Radiology, 81(9): 2231-2245, Sep. 30, 2012.
Manssour et al. "Visualizing Inner Structures in Multimodel Volume Data", Proceedings of the 15th Brazilian Symposium on Computer Graphics and Image Processing (SIBGRAPI'02), Oct. 7-10, 2002, p. 51-58, Oct. 7, 2002.
San Mauro et al. "Nerves of the Heart: A Comprehensive Review With A Clinical Point of View", Neuroanatomy, 8: 28-31, 2009.
Flotats et al. "Proposal for Standardization of 123I-Metaiodobenzylguanidine (MIBG) Cardiac Sympathetic Imaging by the EANM Cardiovascular Committee and the European Council of Cardiology", European Journal of Nuclear Medicine and Molecular Imaging, 37(9): 1802-1812, Aug. 2010.
Wang et al. "Metaiodobenzylguanidine Myocardial Imaging and the Application Thereof", Foreign Medical Sciences, Section of Internal Medicine, 28(5): 081511165-E-1-081511165-E-8, May 2001. & English Translation.
Official Action dated Jan. 6, 2017 From the U.S. Patent and Trademark Office Re. U.S. Appl. No. 14/762,933. (55 pages).
Communication Relating to the Results of the Partial International Search dated Apr. 16, 2015 From the International Searching Authority Re. Application No. PCT/IB2015/050148.
International Preliminary Report on Patentability dated Aug. 6, 2015 From the International Bureau of WIPO Re. Application No. PCT/IL2014/050086.
International Preliminary Report on Patentability dated Aug. 6, 2015 From the International Bureau of WIPO Re. Application No. PCT/IL2014/050088.
International Preliminary Report on Patentability dated Aug. 6, 2015 From the International Bureau of WIPO Re. Application No. PCT/IL2014/050089.
International Preliminary Report on Patentability dated Aug. 6, 2015 From the International Bureau of WIPO Re. Application No. PCT/IL2014/050090.
International Preliminary Report on Patentability dated Dec. 8, 2016 From the International Bureau of WIPO Re. Application No. PCT/IB2015/053984. (11 Pages)
International Preliminary Report on Patentability dated Mar. 17, 2016 From the International Bureau of WIPO Re. Application No. PCT/IB2014/064316.
International Preliminary Report on Patentability dated Mar. 17, 2016 From the International Bureau of WIPO Re. Application No. PCT/IB2014/064319.
International Preliminary Report on Patentability dated Jul. 21, 2016 From the International Bureau of WIPO Re. Application No. PCT/IB2015/050148.
International Preliminary Report on Patentability dated Sep. 24, 2015 From the International Bureau of WIPO Re. Application No. PCT/IL2014/050246.
International Search Report and the Written Opinion dated Oct. 1, 2015 From the International Searching Authority Re. Application No. PCT/IB2015/053984.
International Search Report and the Written Opinion dated Jun. 5, 2014 From the International Searching Authority Re. Application No. PCT/IL2014/050086.
International Search Report and the Written Opinion dated Jun. 9, 2014 From the International Searching Authority Re. Application No. PCT/IL2014/050088.
International Search Report and the Written Opinion dated Jun. 10, 2014 From the International Searching Authority Re. Application No. PCT/IL2014/050089.
International Search Report and the Written Opinion dated May 15, 2014 From the International Searching Authority Re. Application No. PCT/IL2014/050090.
International Search Report and the Written Opinion dated Feb. 20, 2015 From the International Searching Authority Re. Application No. PCT/IB2014/064316.
International Search Report and the Written Opinion dated Feb. 25, 2015 From the International Searching Authority Re. Application No. PCT/IB2014/064319.
International Search Report and the Written Opinion dated Jul. 27, 2015 From the International Searching Authority Re. Application No. PCT/IB2015/050148.
International Search Report and the Written Opinion dated Jul. 28, 2014 From the International Searching Authority Re. Application No. PCT/IL2014/050246.
Invitation to Pay Additional Fees Dated Apr. 10, 2014 From the International Searching Authority Re. Application No. PCT/IL2014/050090.
Invitation to Pay Additional Fees Dated Dec. 16, 2014 From the International Searching Authority Re. Application No. PCT/IB2014/064319.
Invitation to Pay Additional Fees Dated Dec. 23, 2014 From the International Searching Authority Re. Application No. PCT/IB2014/064316.
Supplementary European Search Report and the European Search Opinion dated Jan. 4, 2016 From the European Patent Office Re. Application No. 14743474.0.
Arora "Recent Insights Into the Role of the Autonomic Nervous System in the Creation of Substrate for Atrial Fibrillation—Implications for Therapies Targeting the Atrial Autonomic Nervous System", Circulation: Arrhythmia and Electrophysiology, XP055236980, 5(4): 850-859, Aug. 1, 2012. p. 6, 7, Chapter 'Recent Developments in Imaging of the Autonomic Innervation of the Atria—Implications for AF Ablation'.
Arora et al. "Porcine Intrinsic Cardiac Ganglia", The Anatomical Record Part A, 271A: 249-258, 2003.
Biosensors International Group "D-SPECT™ Cardiac Imaging System", Biosensors International Group, Ltd., Product Description, 2 P., 2013.
Burnstock "Autonomic Neurotransmission: 60 Years Since Sir Henry Dale", The Annual Review of Pharmacology and Toxicology, 49: 1-30, 2009.
Ernst et al. "Image Guided Ablation of Ganglionated Plexi as an Additional to PV Isolation—Follow-Up Results of the Initial Case Series", Heart Rhythm, XP029240122, 12(5/Suppl.): S434-S435, Poster Session V, # PO05-83, May 2015. p. 434, 435, Abstract PO05-83.
Esler et al. "Sympathetic Nerve Activity and Neurotransmitter Release in Humans: Translation From Pathophysiology Into Clinical Practice", Acta Physiologica Scandinavica, 177: 275-284, 2003.
Ghosh et al. "Assessment of Myocardial Ischaemia and Viability: Role of Positron Emission Tomography", European Heart Journal,

(56) References Cited

OTHER PUBLICATIONS

XP055181382, 31(24): 2984-2995, Online Published-Ahead-of Print Oct. 21, 2010. p. 2986, col. 1, p. 2990-2993, col. 2.
Hirsch et al. "Measuring Activity of the Autonomic Nervous System in Humans", Obesity Research, 11(1): 2-4, Jan. 2003.
Hu et al. "Dynamic Molecular Imaging of Cardiac Innervation Using A Dual Head Pinhole SPECT System", Lawrence Berkely National Laboratory, University of California, eScholarship, XP055214624, LBNL Report No. LBNL-60008, p. 1-54, May 23, 2008. Abstract, p. 16, Para 3—p. 20, Para 2, Figs.9, 10, Table 2.
IAEA "Technetium-99m Radiopharmaceuticals: Status and Trends", IAEA, International Atomic Energy Agency Radioisotopes and Radiopharmaceuticals Series, 1: 1-378, 2009.
Knuepfer et al. "Direct Assessment of Organ Specific Sympathetic Nervous System Activity in Normal and Cardiovascular Disease States", Experimental Physiology, 95(1): 32-33, 2010.
Kosa et al. "Principles and Methods of Myocardial Perfusion Imaging", Chap.2: 33-57.
Langer et al. "PET and SPET Tracers for Mapping the Cardiac Nervous System", European Journal of Nuclear Medicine and Molecular Imaging, 29(3): 416-434, Mar. 2002.
Lemery et al. "Feasibility Study of Endocardial Mapping of Ganglionated Plexuses During Catheter Ablation of Atrial Fibrillation", Heart Rhythm, X024972538, 3(4): 387-396, Apr. 2006. p. 395, Left Col., Lines 3-30.
Linz et al. "Atrial Autonomic Innervation: A Target for Interventional Antiarrhythmic Therapy?", Journal of the American College of Cardiology, JACC, p. 1-33, 2013.
Malliani et al. "Emerging Excitatory Role of Cardiovascular Sympathetic Afferents in Pathophysiological Conditions", Hypertension, 39: 63-68, Jan. 2002.
Malpas "Sympathetic Nervous System Overactivity and Its Role in the Development of Cardiovascular Disease", Physiology Review, 90: 513-557, 2010.
Matsunari et al. "Iodine-123 Metaiodobenzylguanidinen Imaging and Carbon-11 Hydroxyephedrine Positron Emission Tomography Compared in Patients With Left Ventricular Dysfunction", Circulation Cardiovascular Imaging, 3: 595-603, Sep. 2010.
Mourot et al. "Effects of the Cold Pressor Test on Cardiac Autonomic Control in Normal Subjects", Physiology Research, 58: 83-91, 2009.
Rabinovitch et al. "A Method of Dynamic Analysis of Iodine-123-Metaiodobenzylguanidine Scintigrams in Cardiac Mechanical Overload Hypertrophy and Failure", Journal of Nuclear Medicine, XP055214626, 34(4): 589-600, Apr. 1993. p. 589, col. 1-p. 593, col. 2, p. 598, col. 2-p. 599, col. 1.
Raffel et al. "Quantification of Cardiac Sympathetic Nerve Density With N-11C-Guanyl-Meta-Octopamine and Tracer Kinetic Analysis", The Journal of Nuclear Medicine, XP055214628, 54(9): 1645-1652, Published Online Jul. 25, 2013. p. 1645, col. 1-p. 1647, col. 1, Figs.1, 2.
Rispler et al. "Quantitative 123I-MIBG SPECT/CT Assessment of Cardiac Sympathetic Innervation—A New Diagnostic Tool for Heart Failure", International Journal of Cardiology, XP028740607, 168(2): 1556-1558, Jan. 17, 2013. p. 1556, col.1-p. 1558, col. 1.
Ross et al. "Research Applications of Selected [123]I-Labeled Neuroreceptor SPECT Imaging Ligands", Journal of Nucelar Medicine and Technology, 32(4): 209-214, Dec. 2004.
Sasano et al. "Abnormal Sympathetic Innervation of Viable Myocardium and the Substrate of Ventricular Tachycardia After Myocardial Infarction", Journal of the American College of Cardiology, 51(23): 2266-2275, Jun. 10, 2008.
Sciagra et al. "Rest-Redistribution Thallium-201 SPECT to Detect Myocardial Viability", The Journal of Nuclear Medicine, XP055181381, 39(3): 384-390, Mar. 1998. p. 384-389, Abstract/39/3/384, p. 384-389.
Sen "Some Observations of Decapsulation and Denervation of the Kidney", The British Journal of Urology, 8(4): 319-328, 1936.
Singh "Chemistry, Design, and Structure-Activity Relationship of Cocaine Antagonists", Chemical Reviews, 100: 925-1024, 2000.
Sisson et al. "Metaiodobenzylguanidine to Map Scintigraphically the Adrenergic Nervous System in Man", The Journal of Nuclear Medicine, 28(10): 1625-1636, Oct. 1987.
Smith "Extrinsic Inputs to Intrinsic Neurons in the Porcine Heart In Vitro", The American Journal of Physiology, 276(2/Pt.2): R455-R467, Feb. 1999.
Smith et al. "Simulation of Cardiovascular System Diseases by Including the Autonomic Nervous System Into a Minimal Model", Computer Methods and Programs in Biomedicine, 86(2): 153-160, May 2007.
Stefanelli et al. "[123]I-MIBG Scintigraphy as a Powerful Tool to Plan an Implantable Cardioverter Defibrillator and to Assess Cardiac Resynchromzation Therapy in Heart Failure Patients", International Journal of Molecular Imaging, XP055214933, 2012(Art. 690468): 1-6, Published Online Sep. 26, 2012. Abstract, p. 1, col. 1-p. 2, col. 1.
Tan et al. "Autonomic Nerves in Pulmonary Veins", Heart Rythm, 4(3 Suppl.): S57-S60, Mar. 2007.
Travin "Cardiac Autonomic Imaging With SPECT Tracers", Journal of Nuclear Cardiology, 20(1): 128-143, Feb. 2013.
Troisi et al. "Relation of Obesity and Diet Sympathetic Nervous System Activity", Hypertension, 17(5): 669-677, May 1991.
University of Ottawa View of NCT02071680 on Feb. 25, 2014: Nuclear Imaging Using 123I-mIBG (Adreview™ GE Healthcare) to Visually Identify Atrial Cardiac Innervation, ClinicalTrials.gov Archive, University of Ottawa Heart Insitute, XP0055214861, 4 P., Feb. 25, 2014. p. 1-3.
Vallabhajosula et al. "Radioiodinated Metaiodobenzylguanidine (MIBG): Radiochemistry, Biology, and Pharmacology", Seminars in Nuclear Medicine, 41: 324-333, 2011.
Vissing et al. "Stimulation of Skin Sympathetic Nerve Discharge by Central Command", Circulation Research, 69(1): 228-238, Jul. 1991.
Wong et al. "Pericardial Fat is Associated With Atrial Fibrillation Severity and Ablation Outcome", Journal of the American College of Cardiology, JACC, 57(17): 1745-1751, 2011.
Zhang et al. "The Celiac Ganglia: Anatomic Study Using MRI in Cadavers", American Journal of Roentgenology, AJR, 186(6): 1520-1523, Jun. 2006.
Supplementary European Search Report and the European Search Opinion dated Jun. 19, 2017 From the European Patent Office Re. Application No. 14841866.8. (11 Pages).
Dilsizian et al. "Current Diagnostic Techniques of Assessing Myocardial Viability in Patients With Hibernating and Stunned Myocardium", Circulation, XP055375410, 87(1): 1-20, Jan. 1993.
Klein et al. "Assessment of Myocardial Viability With Contrast-Enhanced Magnetic Resonance Imaging: Comparison With Positron Emission Tomography", Circulation, XP055375416, 105(2): 162-167, Jan. 15, 2002.
Shabana et al. "Myocardial Viability: What We Know and What is New", Cardiology Research and Practice, XP055375407, 2012(Art. ID 607486): 1-13, Jan. 2012. p. 3, r-h Col., Last Para.
Underwood et al. "Imaging Techniques for the Assessment of Myocardial Hibernation. Report of a Study Group of European Society of Cardiology", ACC Current Journal Review, XP004655395, 13(9): 23, Sep. 2004.

\* cited by examiner

MIBI

Viable
Fibrosis
Scar

DETECTION OF SCAR AND FIBROUS CARDIAC ZONES

RELATED APPLICATIONS

This application is a National Phase of PCT Patent Application No. PCT/IB2015/050148 having International filing date of Jan. 8, 2015 which claims the benefit of priority under 35 USC § 119(e) of from the following applications: U.S. Provisional Patent Application No. 62/030,740 filed Jul. 30, 2014, U.S. Provisional Patent Application No. 61/925,669 filed Jan. 10, 2014, U.S. Provisional Patent Application No. 61/925,670 filed Jan. 10, 2014, U.S. Provisional Patent Application No. 62/003,108 filed May 27, 2014, and U.S. Provisional Patent Application No. 62/030,917 filed Jul. 30, 2014. PCT Patent Application No. PCT/IB2015/050148 is also a Continuation-in-Part (CIP) of PCT Patent Application No. PCT/IL2014/050089 filed Jan. 24, 2014, PCT Patent Application No. PCT/IL2014/050090 filed Jan. 24, 2014, PCT Patent Application No. PCT/IB2014/064316 filed Sep. 8, 2014 and PCT Patent Application No. PCT/IB2014/064319 filed Sep. 8, 2014.

FIELD AND BACKGROUND OF THE INVENTION

The present invention, in some embodiments thereof, relates to detecting zones of fibrous tissue in muscles and, more particularly, but not exclusively, to detecting such zones in the heart, using radioimaging.

Damaged heart tissue is often converted into fibrous tissue, which does not contract or conduct action potentials. Radioimaging techniques are used to image the heart and show as blobs regions where there is no metabolic activity and hence are probably fibrotic.

SUMMARY OF THE INVENTION

There is provided in accordance with an exemplary embodiment of the invention a method of tissue recognition of tissue type in a heart, comprising:
  (i) providing radioactive emission data of cardiac tissue;
  (ii) associating said emission data with a wall of the heart; and
  (iii) analyzing said associated radiation to recognize fibrous tissue in the heart wall. Optionally, said providing comprises injecting a patient with a radioactive tracer; and collecting radiation emitted from cardiac tissue. Optionally or alternatively, said analyzing comprises categorizing a shape of a fibrous zone in said heart wall. Optionally or alternatively, said analyzing comprises identifying one or more gaps between fibrous zones in said heart wall. Optionally, said identified gap is smaller than 5 mm in minimal width.

In an exemplary embodiment of the invention, said analyzing comprises identifying one or more elongate fibrous zones in said heart wall. Optionally or alternatively, said analyzing comprises identifying one or more non-convex fibrous zones in said heart wall. Optionally or alternatively, said analyzing comprises identifying one or more circumferential fibrous zones in said heart wall. Optionally or alternatively, said analyzing comprises identifying one or more fibrous zones with a maximal extent of less than 30 millimeters. Optionally or alternatively, said analyzing comprises identifying one or more fibrous zones caused by medical ablation.

Optionally or alternatively, said analyzing comprises identifying at least three non-contiguous fibrous zones in said heart wall. Optionally or alternatively, said analyzing comprises identifying one or more fibrous zones in an atrial wall. Optionally or alternatively, said analyzing comprises identifying one or more fibrous zones that do not reach a full wall thickness. Optionally or alternatively, said analyzing comprises identifying one or more fibrous zones that are inside a wall. Optionally or alternatively, the method comprises generating an image of fibrous zones in at least a portion of said heart. Optionally, said image has a resolution of better than 5 millimeters. Optionally or alternatively, said image distinguishes between fibrous tissue in different layers of the heart wall. Optionally or alternatively, said image distinguishes between different degrees of fibrosis. Optionally or alternatively, said generating comprises normalizing said emission data non-uniformly for different sections of said wall. Optionally or alternatively, the method comprises overlaying additional data on said image. Optionally or alternatively, the method comprises using said image for real-time navigation in the body.

In an exemplary embodiment of the invention, said tracer includes one or more of Tc-99, I-123 and Thalium-201.

In an exemplary embodiment of the invention, said analyzing comprises assessing a risk for atrial fibrillation. Optionally or alternatively, said analyzing comprises assessing a risk for ventricular arrhythmia. Optionally or alternatively, said analyzing comprises planning a correction of an ablation procedure.

In an exemplary embodiment of the invention, said associating comprises using a model of said wall. Optionally, said model is generated from a structural image of said heart.

In an exemplary embodiment of the invention, at least some of said fibrous tissue is identified as non-viable tissue.

In an exemplary embodiment of the invention, at least some of said fibrous tissue is identified as viable tissue mixed with fibrous tissue.

There is provided in accordance with an exemplary embodiment of the invention, a method of cardiac imaging, comprising:
  (i) injecting a patient with a radioactive tracer;
  (ii) collecting radiation emitted from cardiac tissue;
  (iii) associating said collected radiation with an atrial or ventricle wall of the heart;
  (iv) generating an image of a distribution of said tracer in said atrial wall; and
  (v) displaying at least one fibrous zone in said wall. Optionally, said generating comprises generating a map of fibrous and non-fibrous zones in said cardiac tissue.

There is provided in accordance with an exemplary embodiment of the invention, a method of tissue recognition of tissue type in a body tissue, comprising:
  (i) providing radioactive emission data of the tissue;
  (ii) associating said emission data with a segment of regular tissue structure of the organ; and
  (iii) analyzing said associated radiation to recognize fibrous tissue within the segment. Optionally, said segment is a part of the stomach wall.

There is provided in accordance with an exemplary embodiment of the invention, a method of generating a display of at least a section of an organ, comprising:
  (a) providing spatially arranged data relating to a property of said segment; and
  (b) normalizing said data according to a potential of causing of a pathology based on said data and/or based on other data.

There is provided in accordance with an exemplary embodiment of the invention, a method of generating a display of at least a section of an organ, comprising:

(a) mapping a functional property of said section using NM (Nuclear Medicine) imaging;

(b) mapping an electrical property of at least part of said section; and (c) generating a map of a function of said functional property and said electrical property.

There is provided in accordance with an exemplary embodiment of the invention, a display showing a map of NM data of a tissue section normalized according to an electrical property of the tissue.

There is provided in accordance with an exemplary embodiment of the invention, a display showing a map automatically generated from measurements of a heart and showing a probability of reentrancy per location.

There is provided in accordance with an exemplary embodiment of the invention, a non-volatile data storage having thereon an image of the heart showing fibrous zones with a resolution of better than 5 mm.

There is provided in accordance with an exemplary embodiment of the invention, apparatus for image generation, comprising:

(a) a model storage;

(b) an emission associater which associates radioactive emissions with a part of said model; and (c) an image generator which reconstructs an image of fibrous portions of a heart wall using said associated emissions.

There is provided in accordance with an exemplary embodiment of the invention, apparatus configured to perform the methods, at least post injection and/or acquisition, as described herein.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system."

Furthermore, aspects of the present invention may take the form of a computer program product embodied in one or more computer readable medium(s) having computer readable program code embodied thereon. Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced. Color images are provided to better illustrate various tissue characteristics.

In the drawings.

DESCRIPTION OF SPECIFIC EMBODIMENTS OF THE INVENTION

Figure 1:
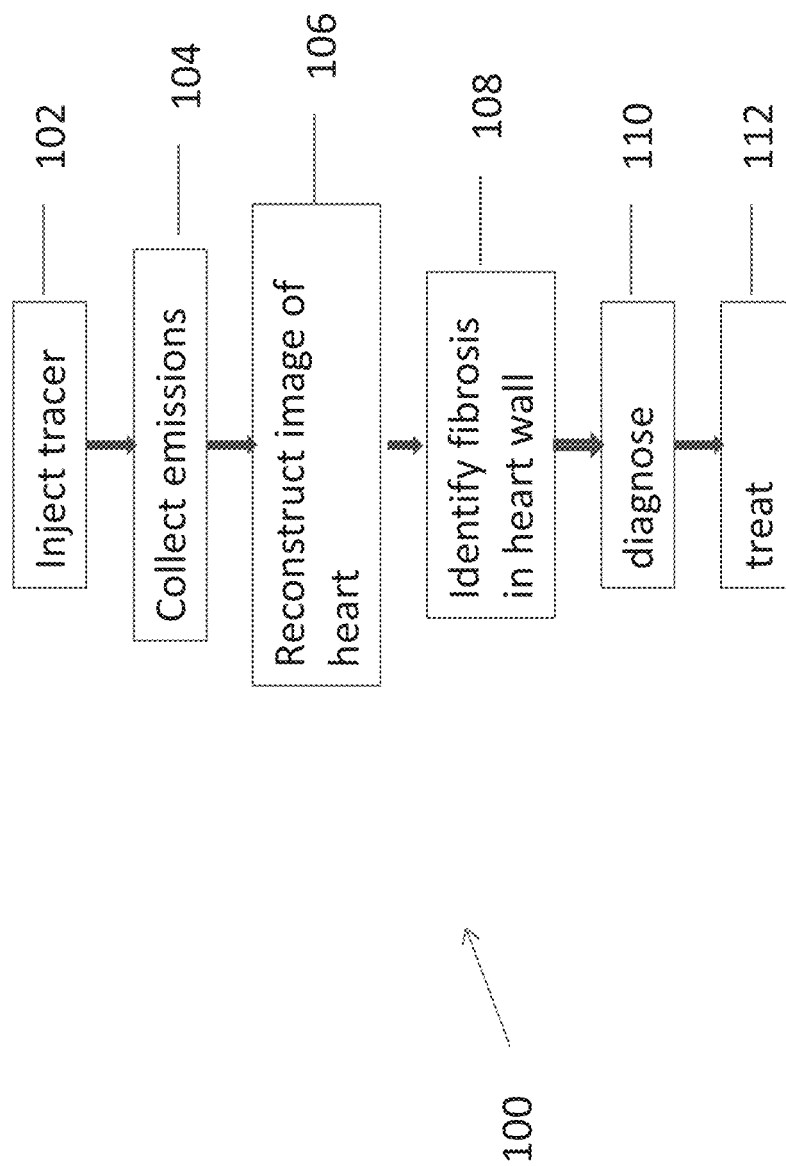
FIG. 1 is a flowchart of a method of detecting fibrous zones in a heart, in accordance with exemplary embodiments of the invention.

The present invention, in some embodiments thereof, relates to detecting zones of fibrous tissue in muscles and, more particularly, but not exclusively, to detecting such zones in the heart, using radioimaging.

Overview

An aspect of some embodiments of the invention relates to detecting of fibrosis in the walls of a heart, using radioimaging. In an exemplary embodiment of the invention, the detected fibrotic regions are in addition to any scar areas that are a result of the healing of an infract. For example, the detection can be at a high resolution, such detecting regions with a width of less than 10 mm, regions that do not include the entire thickness of a wall and/or regions in the wall of the atria. Optionally, the resolution of delineation of fibrotic regions is better than 5 mm, better than 3 mm, or better than 1 mm. Optionally or alternatively, shapes other than blobs are detected. For example, elongate shapes are detected. Optionally or alternatively, a layer in the cardiac wall which has fibrosis is detected, for example, endocardial, mid-myocardial and/or epicardial. In some exemplary embodiments of the invention, a degree of fibrosis (less than 100% scar tissue) is detected.

In some exemplary embodiments of the invention, the detected zone or regions are used to assess previous ablation activities performed in the heart. Optionally, gaps in such ablations are determined, and a new ablation aimed at one or more such gaps is optionally performed. Optionally or alternatively, the degree and/or layout of fibrosis in an atrium is used to assess risk for atrial fibrillation. Optionally or alternatively, the layout of fibrotic areas in a chamber are used to assess risks in the chamber, for example, risk of arrhythmia and/or risk of reduced cardiac output and/or aneurysm.

In some embodiments, the methods described herein are used for other organs, for example, muscular organs, for example, the stomach. Optionally, adhesions in the abdominal cavity or scar tissue (or other non-active tissue type) in other tissue, for example muscles, joints and/or the liver is detected. It is a particular feature of some embodiments of the invention that a high enough resolution of fibrosis is detected that a non-binary characterization of tissue can be carried out.

An aspect of some embodiments of the invention relates to imaging the wall of the atria using radioimaging. In some exemplary embodiments of the invention, the atria is imaged by first providing a model of the atria, for example, collected using CT imaging, and then selecting from the radioimaging data emissions that originate from an area indicated in the model as belonging to the atria. In some exemplary embodiments of the invention, this may allow imaging the metabolic activity of the left atria and/or the right atria. Optionally, this is used for the viewing of fibrous zones and scars in the atria.

An aspect of some embodiments of the invention relates to a system which receives as input anatomical data and functional data and outputs a map indicating fibrosis thereon. Optionally, a model of, for example, wall thickness, is used to constrain emissions to an organ section and provide a better indication of low emission sections thereof.

An aspect of some embodiments of the invention relates to generating a diagnosis and/or treatment and/or diagnosis plan based on a map of fibrosis tissue. In an exemplary embodiment of the invention, the map is analyzed to detect regions in risk of causing and/or supporting arrhythmia. Optionally or alternatively, the map is analyzed to determine which of several treatments may better work.

An aspect of some embodiments of the invention relates to normalizing one set of data by another set of data. In some exemplary embodiments of the invention, one set is NM data and the other set is EP data or geometrical data extracted from the NM image. In some exemplary embodiments of the invention, normalization indicates a probability of pathology.

In one example, NM data indicating fibrosis is normalized using EP data of, for example, refractory period, or estimated conduction velocity (e.g., estimated from a width of conduction pathway and/or degree of fibrosis). The normalized image may be used to indicate a probability of reentry circuit existing at a point; or, in some embodiments, potential for another pathology, such as susceptibility to fibrillation or to being an ectopic source of arrhythmia.

In an exemplary embodiment of the invention, a location may be more probably to be pathological if it is pathological both with respect to the degree of fibrosis (e.g., not 0% or 100%) and abnormal electrical properties.

In some cases normalization goes beyond reduction of noise or correction for differences in amount of tissue or detection. For example, as described below, normalization may correct for different tissue behavior and/or expected behavior.

Also, normalization may be, mathematically more complex than multiplication.

For example, normalization may include fitting to a window before multiplication or setting of maximum or minimum values. Also, as described herein, for example, normalization can be of a statistical property, such as standard deviation.

In some cases, the analysis of the data to generate an image goes beyond normalization, for example, applying one or more rules, tables and/or functions to translate NM data and/or EP data and/or other data into a display showing information regarding, for example, fibrosis and/or susceptibility to disease.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Exemplary Detection Process

Referring now to the drawings, FIG. 1 is a flowchart 100 of a method of detecting fibrous zones in a heart, in accordance with an exemplary embodiment of the invention.

At 102 a radioimaging tracer, for example Sestamibi, Tetrafosmine and/or Thallium, may be injected or otherwise provided into the body, to be taken up by metabolizing cardiac tissue. Alternatively, a patient with a radioactive tracer therein may be provided.

At 104, radioactive emissions from the body may be collected, for example, using a functional imaging modality, for example, SPECT or PET, for example using a D-SPECT camera, sold by Biosensor International Group, Bermuda.

At 106, an image of the heart or an area within the heart, including heart walls may be reconstructed from the emissions. The method described in FIG. 3A may be used, for example. The area may be determined based on a model of the atria, for example as collected using a structural modality, e.g., CT.

At 108, portions of heart walls that are fibrotic may be identified or otherwise detected or localized, for example, based on a lack of uptake (and hence emission from such portions. In some embodiments, the fibrotic portions may be determined based on their size, shape and/or location. In some embodiments, a map showing fibrotic portions and non-fibrotic portions is optionally displayed (or otherwise provide) to an operator, e.g., a physician.

In an exemplary embodiment of the invention, the shape, size and/or placement or other geometric properties of the identified zones are analyzed. Optionally, the analysis includes categorization of the detected zones. For example, categorization may include one or more of "gap in ablation", "ablation scar", fibrous tissue (e.g., intermixed with viable tissue)" and/or "potential reentrant zone".

In an exemplary embodiment of the invention, the shape, size and/or placement and/or other geometric properties of the identified zones are analyzed. Optionally, the analysis includes categorization of the detected zones. For example, categorization may include an analysis demonstrating the transmurality of the fibrous tissue and/or an analysis identifying a "gap" in the depth of the tissue. It is believed that currently there are no recognized means to test, in a non-destructive way, the transmurality of a fibrous lesion inside the myocardium thickness. This feature has the potential benefit of being used in detecting and guiding treatment of arrhythmia originating from intra-wall lesions, e.g., of the ventricles.

At 110, a diagnosis of the heart is optionally performed.

At 112, treatment (e.g., ablation and/or drugs), optionally based on the diagnosis, is optionally provided.

Exemplary Cardiac Fibrosis Layouts

Figure 2A:
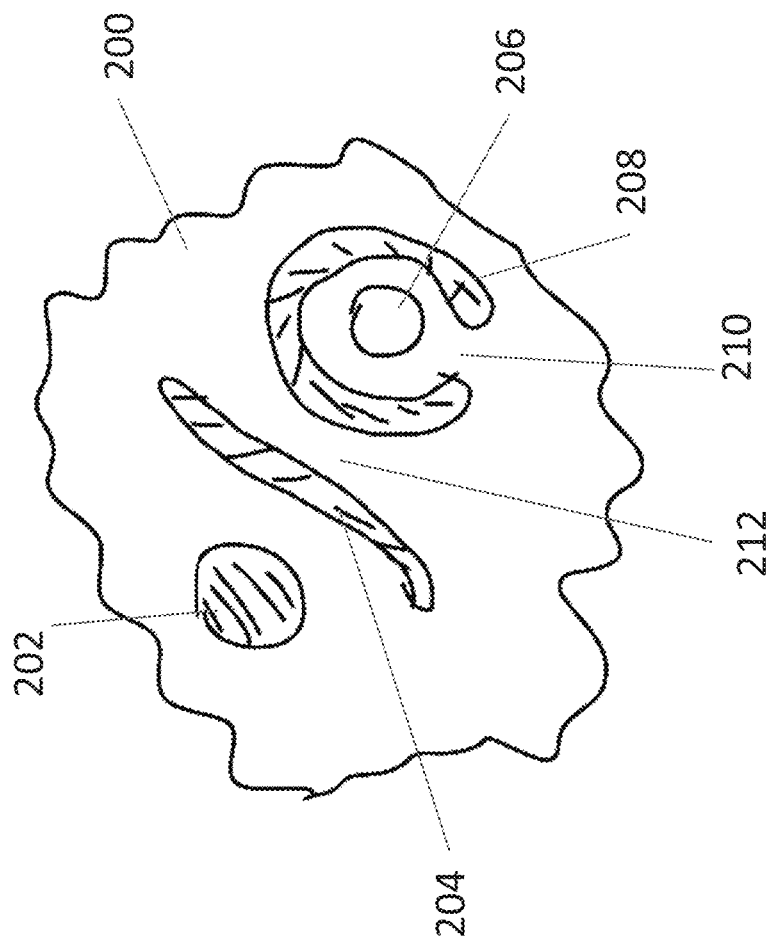
FIG. 2A is a schematic showing of a heart muscle segment showing fibrous and non-fibrous zones, along a muscle, which are detectable in accordance with some embodiments of the invention.
Figure 2B:
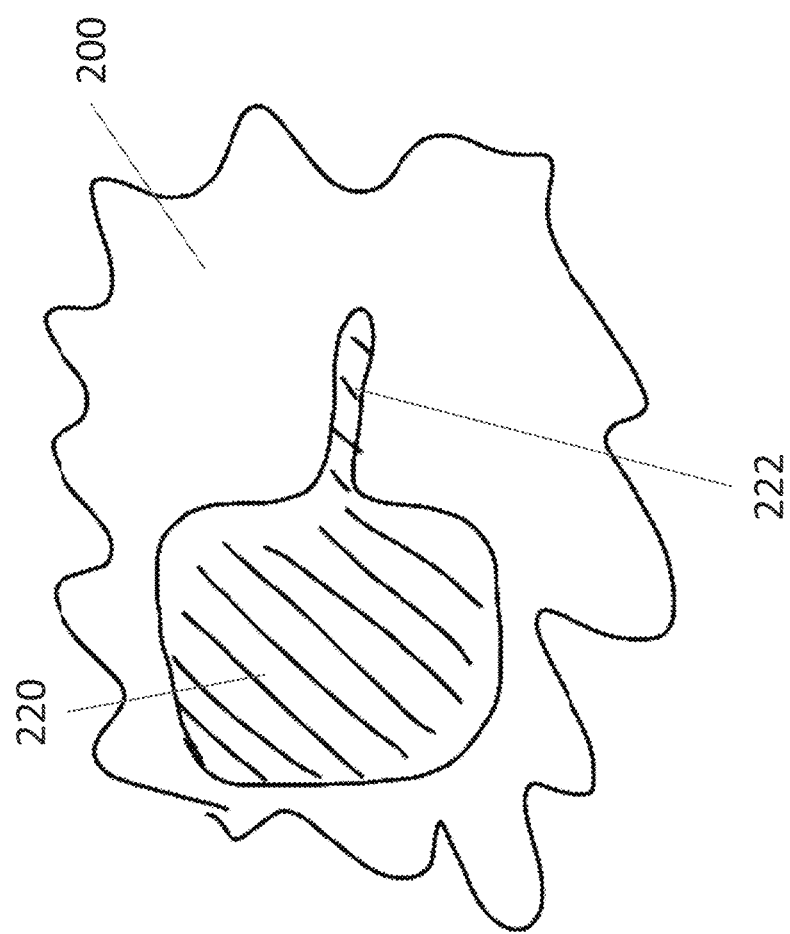
FIG. 2B is a schematic showing of a heart muscle segment showing additional examples fibrous and non-fibrous zones, along a muscle, which are detectable in accordance with some embodiments of the invention.
Figure 2C:
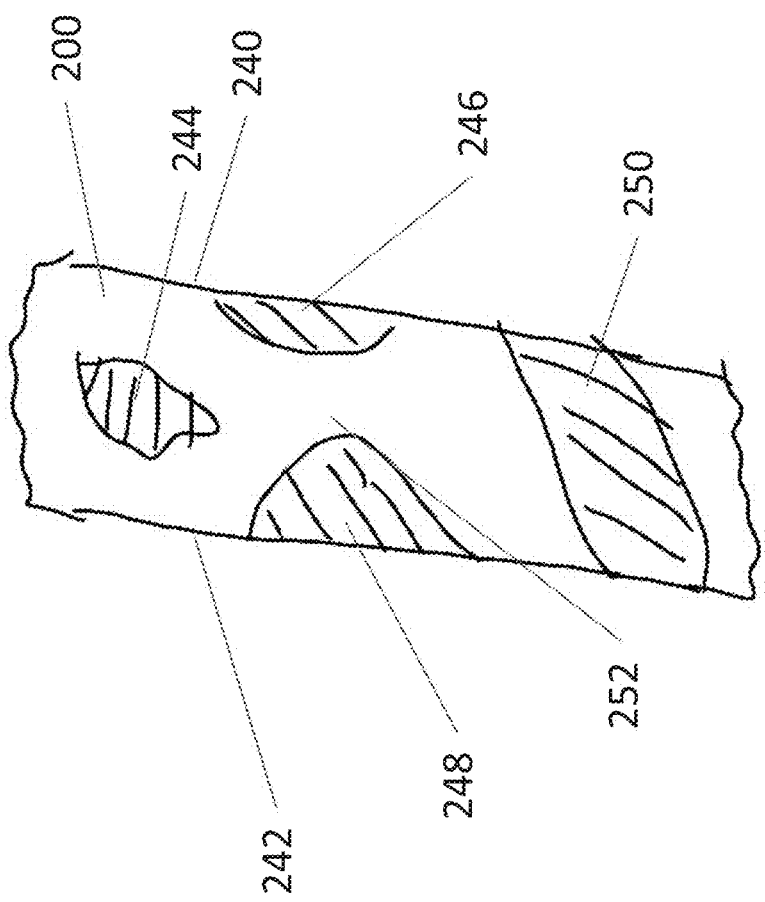
FIG. 2C is a schematic showing of a heart muscle segment showing fibrous and non-fibrous zones in cross-section of a muscle, which are detectable in accordance with some embodiments of the invention.

FIGS. 2A-2C illustrate various exemplary layouts of fibrotic tissue in the heart, as may be detected in accordance with some embodiments of the invention.

FIG. 2A is a schematic showing of a heart muscle segment 200 showing exemplary fibrous and non-fibrous zones, along a muscle, which are detectable in accordance with some embodiments of the invention. Muscle segment 200 may be, for example, part of an a atrial wall, such as the left or right atria, part of a ventricular wall, such as the left or right ventricle and/or part of a septum, such as a trans-ventricular septum, a trans-atrial septum or an atrial-ventricle septum. The zones are exemplary and need not be found in the number size and/or combination shown.

A first type of fibrosis is a small region 202, for example in the general shape of a circle, which may be, for example, the scar of a previous ablation. Optionally, region 202 is between 2 and 20 mm in maximal extent, for example, between 2 and 10 mm or between 1 and 5 mm. In some cases, region 202 is a reaction to an implanted electrode or other component.

A second type of fibrosis is an elongate region 204, which may also be a scar of a previous ablation. In an exemplary embodiment of the invention, the elongate region has a width of less than 20 mm, less than 15 mm, less than 10 mm, less than 5 mm or intermediate widths and is visible in the reconstructed image. In an exemplary embodiment of the invention, the ratio between visualized maximum length and visualized minimum width is between 3:1 and 20:1 or 40:1.

A third type of fibrosis is a circular zone 208, which, for example, can be an ablation scar of an ablation around a pulmonary vein (or other vessel) 206. As shown, a gap 210 is formed in an otherwise circumferential zone 208. For example, the width of the gap may be between 1 and 20 mm, for example, between 1 and 10 mm, for example, between 1 and 5 mm.

Also visible is a zone of non-fibrous tissue 212, between fibrous zones 204 and 208, which zone can be identified in the image and may serve as a conduction pathway for action potentials.

While not shown, other fibrous zones are found in the heart, for example, the annulus of a valve and/or various types of congenital pathologies.

A particular feature of some embodiments of the invention is the association of the location of the fibrous tissue with concomitant damage due to its existence. For example, a nervous fiber passing through an area of the heart that suffered a prolonged ischemia and as a result developed a transmural fibrous body and/or prevent blood flow to the nerve, may destroy the nervous fiber. Optionally, the effect of such destruction is estimated, for example, based on the behavior of the heart and/or based on the anatomy of the heart. Optionally or alternatively, a second imaging tracer, which is selectively uptaken by nervous tissue, such as mIBG is used to detect regions with reduced innervation. It is hypothesized that the area of denervation and/or its border with the area of the innervation is prone and/or its border with fibrous and/or dead tissue sometimes act as substrate for generation and/or maintenance of various cardiac arrhythmia, which may be due to the expected dispersion of electrical properties found at the co-location of innervated and denervated myocardium.

FIG. 2B is a schematic showing of a heart muscle segment showing additional examples of fibrous and non-fibrous zones, along a muscle, which may be detectable in accordance with some embodiments of the invention. A zone 220 is generally of a size and shape to be visualized, at least in the left ventricle, using standard radioimaging techniques. Such techniques may allow large, generally convex fibrous regions to be identified in the left ventricle, but do not include information regarding what layer of the heart wall is or is not affected. In addition, if the shape includes non-blog sections, such as an elongate extension 222, these will not be visible. However, in some embodiments of the invention, visualization allows the edge of a large scar area to be identified, including, for example, various extensions. In an exemplary embodiment of the invention, the resolution of imaging is better than 10 mm, 5 mm, 3 mm or 1 mm in along the muscle wall and/or through the thickness of the muscle wall.

Optionally, the extension includes portions that are less than 20%, 10%, 5% or intermediate percentages of a minimal dimension of the blob (e.g., generally convex) portion of the fibrous zone. In an exemplary embodiment of the invention, non-convex portions of a blob are detected. Optionally or alternatively, fibrous zones which cannot enclose a circle 30 mm (or 20 mm or 10 mm or smaller or intermediate sizes) in diameter are detected.

FIG. 2C is a schematic showing of a heart muscle segment showing fibrous and non-fibrous zones in cross-section of a muscle, which may be detectable in accordance with some embodiments of the invention. In the figure, reference 240 indicates a first surface and reference 242 a second surface of the heart wall. Some walls, such as the exterior left ventricle wall, have an endocardial side (e.g., 242) and an epicardial side (e.g., 240). Other walls, such as a ventricular septum, have both surfaces inside the heart. Optionally, three general layers are identified in the wall: near surface 242, near surface 240 and in-between. In some wall, a greater number of regions are distinguished. This is especially so in portions such as the septal wall, which may have multiple internal layers with different innervation sources and/or different blood delivery pathways (e.g., 3 layers). In any case, some embodiments of the invention may give a millimeter accuracy of a fibrous zone, while allowing for more than three layers, and the use of three or other number such as four or five layers is a simplification which may make diagnosis easier, even if less precise.

In an exemplary embodiment of the invention, the different functions of the different layers are taken into account when estimating an effect of a fibrous region.

For example, the inner layer of the heart (endocardium) is well known to be sensitive to ischemia and to have an abundance of parasympathetic fibers, while the outer layer of the heart (epicardium) is well known to have abundance of sympathetic fibers. Damage to only one of the layers may cause a reduced ability to provide excitatory or inhibitory modulation by the nervous system and may suggest (e.g., for diagnosis) different types of pathologies which may be caused thereby and/or treated thereby (e.g., by further ablation or other methods as described below).

A fibrous zone 244 is wholly inside the muscle. In some patients, this means that while contraction may be impaired, no effects on conduction are expected. In some exemplary embodiments of the invention, measurement of the relative thickness of muscle 200 and zone 244 is provided. Optionally or alternatively, measurement of the space between the zone and surfaces 242 and/or 244 is provided.

A zone 246 is located on one surface. If this is an outer surface, then the zone may be the result of damage other than by ablation. Such a zone may also indicate damage to a nearby nervous ganglion. Such damage may be verified using imaging methods such as described in U.S. provisional application No. 61/831,664, filed Jun. 6, 2013 and titled "NERVE VISUALIZATION AND TREATMENT", the disclosure of which is incorporated herein by reference.

A zone 248 may be adjacent an inner surface, which may indicate, for example, damage due to ablation. That the ablation does not cross the entire thickness of the wall may indicate an unsuccessful ablation. A gap 252 between fibrous zones and/or between a zone and the other muscle surface may, for example, indicate such a gap, indicate an amount of viable muscle and/or otherwise indicate a conduction pathway, even in a muscle segment which is no-conducting on its surface. It is noted that such areas may act as an arrhythmia foci of or a part of an arrhythmia loop.

Further ablation thereof is desirable in some cases, with the location of viable tissue guiding, for example, ablator location, power, type and/or sequence.

A zone 250 shows a complete surface to surface fibrotic zone. In some cases, ablation is planned to not reach from surface to surface and a zone 250 may indicate the potential for ablation damage outside the heart muscle, desired or undesired.

As can be appreciated, an image of the heart can include multiple such zones and the resolutions described above may also be provided for a set of zones and the spacing between.

Figure 2D:
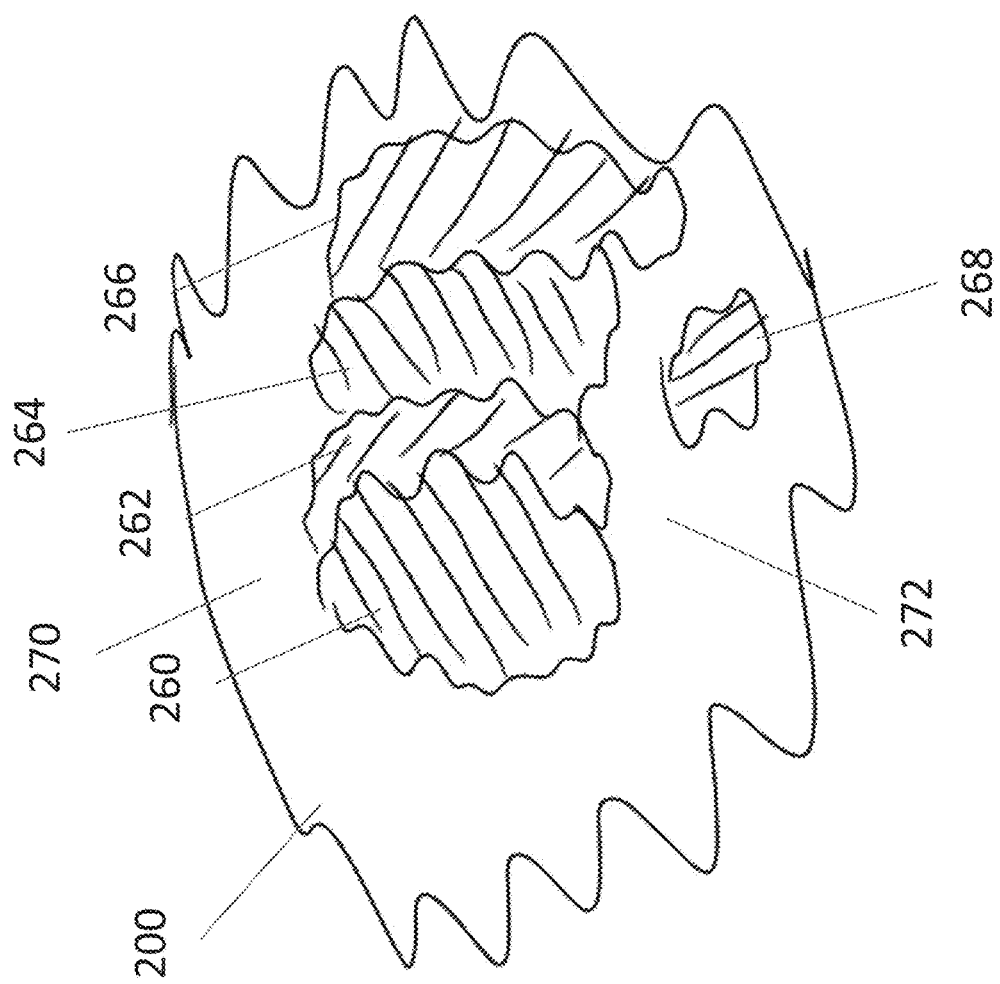
FIG. 2D is a schematic showing of a heart muscle segment showing fibrosis near scar tissue of a muscle, which are detectable in accordance with some embodiments of the invention.

FIG. 2D is a schematic showing of a heart muscle segment (200) showing fibrosis near scar tissue of a muscle, which are detectable in accordance with some embodiments of the invention. The right angled sections (260, 264) indicate sections with total transmural scaring (e.g., due to infarct or ablation). The left angled sections (262, 266, 268) indicate areas with only partial scarring, for example, areas with fibrosis, in which, in a given layer (possibly the entire thickness of muscle) there is a intermixing of living and fibrotic tissues. Tissue with fibrosis may be able to contract and/or conduct an action potential. However, due to the intermixing of living and dead tissue, such fibrosis may be the source and/or sustainer of arrhythmia (e.g., due to long pathways and/or slowly conducting tissue therein). In some embodiments of the invention fibrosis may be detected using analysis of NM data and optionally verified using electrical measurements (e.g., with a catheter). In an exemplary embodiment of the invention, detection of fibrosis includes estimating degree of fibrosis, optionally a non-binary degree. For example, a semi-scar region may be identified as containing 10%, 30%, 50%, 60%, 80% or intermediate or larger percentages of fibrotic tissue.

Optionally, at least 2, 3, 4, 5 or more graduations between "non-fibrotic" and "100% scar tissue" are provided by the imaging and/or analysis system, for example, as described herein.

FIG. 2D shows an example where a conduction pathway (e.g., via section 262) exists between a location 270 and a location 272. Such a pathway, on its own, or together with another pathway (e.g., via 266) may cause arrhythmia. In one example, sections 260-266 are created by ablation and areas 262 and 266 are supposed to be scar tissue and non-conducting. A possible treatment is to ablate across section 262 or otherwise bridge between sections 260 and 264 so as to cause total scaring in a least a part thereof. Another possible treatment is to ablate around sections 260, 262 and 264.

Reference 268 indicates a standalone fibrosis area. It is noted that fibrosis can also be an indication of progression of heart disease. Optionally, areas such as 268 are mapped to detect change in size, shape and/or number over time. Optionally, treatment is by drugs and, optionally, to prevent arrhythmia, ablation of area 268.

It should be appreciated that a real heart may have a mixture of geometries such as shown in FIGS. 2A-2D. In particular, some regions may be scarred transmurally or partially transmurally, while others have fibrosis for part or all of a tissue thickness. A single section of muscle may also have a graduation from total scar tissue to fibrosis. It is also note that conduction layers may be alive or dead, and may be detected, for example, as described below. It is noted that, typically, damage is contiguous and does not skip layers. This may be used to assist in diagnosis.

In an exemplary embodiment of the invention, non-transmural scar tissue is differentiated from fibrosis using one of two methods. In some embodiments, imaging uses a fine enough resolution so that viability of separate layers can be identified. In some embodiments, an electrical measurement (e.g., conduction velocity) is used to see if there is any residual tissue activity.

Exemplary Fibrosis Detection

Figure 3A:
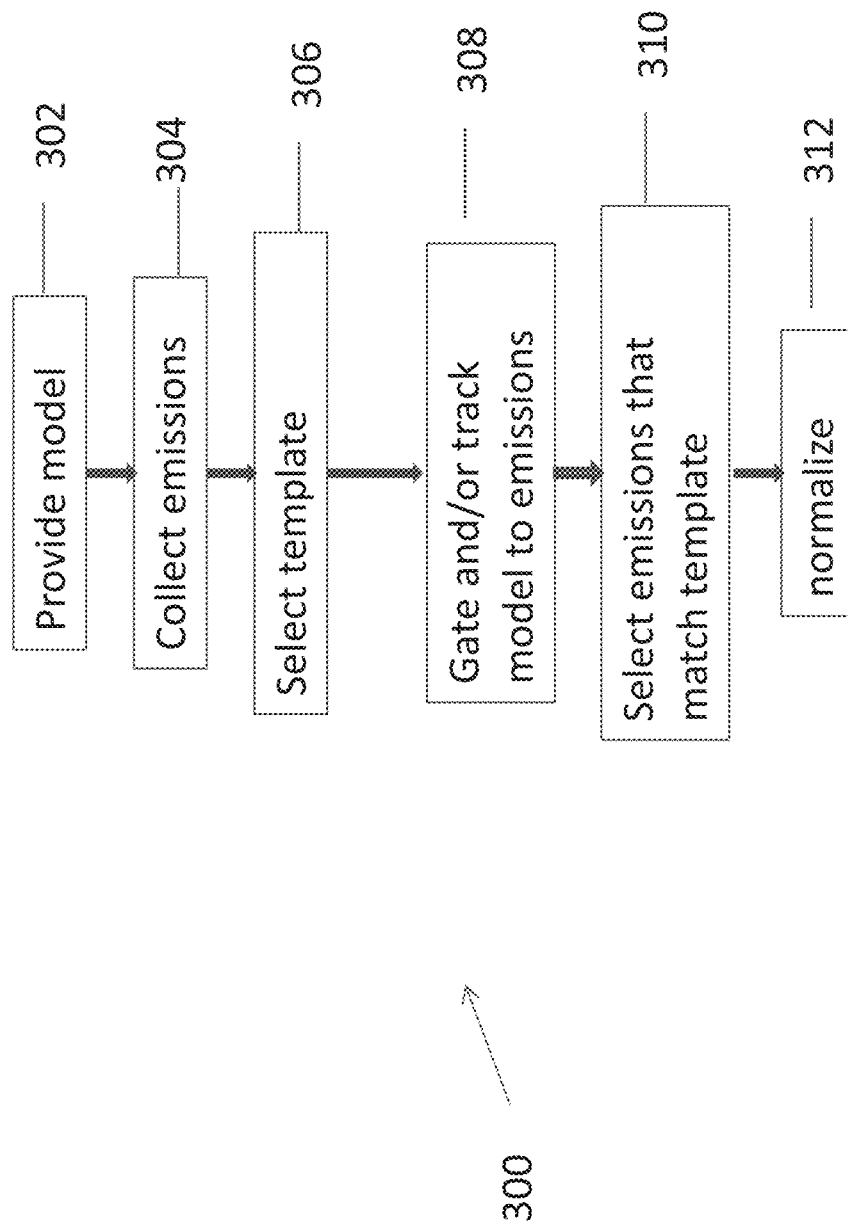
FIG. 3A is a flowchart of a method of radioimaging data processing, in accordance with some exemplary embodiments of the invention.

FIG. 3A is a flowchart 300 of a method of radioimaging data processing, in accordance with some exemplary embodiments of the invention, which uses a model of the heart to localize radiation emissions to heart walls. While in some embodiments of the invention, the method showing in US patent application publication 2009/0201291, the disclosure of which is incorporated herein by reference, is used, in others, a different method, for example the following method, may be used.

At 302 a model of the heart is optionally provided. Such a model is optionally generated using a structural modality, e.g., a CT imager. In some exemplary embodiments of the invention, the model is a 4D model which includes different shapes for different parts of the cardiac cycle.

At 304, radioactive emissions may be collected from the body. This may be done, for example, before, during and/or after model provision. Optionally, the data acquisition is binned or gated according to cardiac cycle (e.g., using an ECG sensor to indicate state in cycle). In an exemplary embodiment of the invention, radioactive emissions are collected following injection of a radioimaging tracer, for example Sestamibi, into the body.

At 306, a template for reconstructing the heart wall may be selected and/or otherwise generated. 306 may be carried out before, during and/or after data (e.g., radioactive emissions) collection. In some exemplary embodiments of the invention, the template is an oversize template, for example, redefining the wall thickness to be a factor of between 1.1 and 2 of the thickness indicated in the model. In some exemplary embodiments of the invention, this factor is a function of the thickness of an imaged (e.g., reconstructed nuclear image) portion of the heart. For example, the template thickness of the left ventricle is set to be a factor of about 1.2 of the thickness of the left ventricle. Optionally or alternatively, the thickness of the right ventricle wall is set to be a factor of about 0.7. Factors of about 0.5 are optionally used for the atrial walls.

It is noted that these factors are generally oversize with respect to the true wall thickness.

In some exemplary embodiments of the invention, the template is generated defining a first shape which fits inside the model and defining a second shape which encloses the model and defining the template (walls of interest) as lying between the two shapes.

At 308, a correspondence between the template and the emission data is optionally provided. For example, such a correspondence may be 3D or 4D. Optionally, the template is resized and registered to match the apparent size of the heart. Optionally, this resizing uses one or more landmarks in the heart, for example, the left ventricle, which are acquired by reconstructing an image of the heart using the acquired emission data. Optionally or alternatively, other registration cues are used, for example, the right ventricle, the liver or torso. Optionally or alternatively, an iterative reconstruction process is used with an initial guess for the template registration being provided (e.g., manually) and then the reconstruction is repeated to converge on the template.

In one example, an average image (average between diastole and systole) is computed and used for registration.

In one example, the image (and/or model) of the heart is manually segmented, for example, to indicate the left atria.

At 310, emissions from locations matching the template are selected and optionally used to reconstruct an image. If the template is 4D, a 4D image is optionally reconstructed. Optionally, for analysis, a series of images of the heart are integrated, for example, averaged, with the model being used to define a mapping between different parts of the images at different times. The nuclear image may or be converted or overlaid with a map of fibrous and non-fibrous zones. The image may displayed (and/or otherwise be provided) to an operator, e.g., a physician.

At 312, the values of the image are optionally normalized along a scale between maximum and minimum. In some embodiments, the image is optionally normalized with an average value of emissions in the heart or a portion of the heart. A threshold is optionally defined (e.g., 30%, 15%, 10% or smaller or intermediate percentages), below which an area is assumed to be non-active. In some embodiments, the normalized image may be displayed to an operator.

In an exemplary embodiment of the invention, the normalization is per layer of the heart wall.

In an exemplary embodiment of the invention, normalization is area dependent, for example, based on an expected muscle wall thickness (e.g., a higher threshold for left ventricle wall than for left atrial wall). Optionally or alternatively, normalization is personalized, for example, based on demographics or previous disease or treatment.

Optionally or alternatively, normalization is local, for example, normalizing tissue measurements according to measurements in nearby tissue (e.g., same chamber, same wall, and/or distance smaller than, for example, 3 or 2 cm). Local normalization may assist in detecting local variations in tissue viability. In some exemplary embodiments of the invention, statistical measures of variance, for example, standard deviation, are used to identify parts of the heart with extreme values of signal, for example, areas that are very active or areas that appear dead or near dead. In some cases, frequency (or wavelet or template matching) analysis or other types of statistical and/or image processing methods are used to detect parts of the tissue with sharp changes in value and/or with non-monotonic local changes (e.g., indicating a patchwork of viability).

In some exemplary embodiments of the invention, normalization is acquisition dependent. For example, image acquisition may be less sensitive at some locations, and the threshold adjusted accordingly. For example, tissue which is located where the imager is less sensitive or places where the tissue moves more (some counts may not be correctly attributed) may have a lower threshold and/or higher normalization value. In an exemplary embodiment of the invention, a lower threshold and/or higher normalization is expected for the base of the heart.

In an exemplary embodiment of the invention, the amount of noise is used as a proxy for estimation of amount of unattributed counts, indicating that a different normalization and/or threshold be used.

Optionally or alternatively, the signal level attributed to the blood in the heart chamber is subtracted from the wall signals and/or otherwise used for normalization.

In one example, heart wall with emission levels at below a threshold generated from the signal level attributed to blood, is considered scar tissue. Higher levels are optionally depicted as fibrosis and/or non-fibrotic.

In some exemplary embodiments of the invention, normalization takes into account that the activity pattern in a heart is non-uniform, even if corrected for wall thickness and sensitive. For example, left ventricular muscle may be assumed to have more metabolic activity than right atrium muscle.

In some exemplary embodiments of the invention, normalization takes into account electrical properties and/or a degree of pathology of a measured property. For example, differences in the conduction velocities and/or refractory periods of the imaged heart wall tissue (e.g., determined using EP (electro-physiology) mapping, for example, using the Carto® system, of an EP catheter with a position sensing system for detecting the position of the catheter tip) may be used to normalize a fibrosis image. This normalization takes into account the fact that fibrosis zones are non-conducting and that narrow viable tissue between fibrosis zone typically conduct slower than wide viable tissue. Optionally, a corresponding estimate may be made based on the refractory map. In some embodiments of the invention, an assumption is made that all refractory periods are identical (e.g., refractory map is uniform). In some embodiments and/or for a second level of analysis an assumption of dependency of path size and/or shape on refractory period and/or conduction velocity is made. For example, it is assumed that there is a relative shortening of a refractory period that is dependent on length and/or width of the conduction path. Optionally, a new map is generated showing (e.g., color coded) the reentrant probability of a substrate.

Optionally, such a map also takes into account a reactivity and/or a degree of control of the tissue (e.g., tissue has less control if nervous control thereto is damaged and may have a larger reactivity due to reaction to damage or if it is controlled by highly active ganglions).

In some exemplary embodiments of the invention, normalization takes into account differences in activity patterns according to levels of physical activity and/or stress (e.g., having different normalization maps for different conditions).

Optionally, a user can select which normalization method to use for display and/or indication of potentially problematic areas.

In an exemplary embodiment of the invention, normalization uses a model of the heart in which each region (e.g., 2, 3, 5, 10, 15, 30 or intermediate or greater number of regions) has a different value for at least one normalization parameter (e.g., one or more of gain, noise level, wall thickness, maximum cutoff, zero value and/or voxel dimensions) and/or normalization method. In an exemplary embodiment of the invention, normalization is applied by aligning the model with the acquired data and applying the corresponding parameters.

In some embodiments of the invention, the model is personalized, for example, based on known patient pathologies and/or a previous measurement of the patient. For example, a dead zone in a previous NM image or ECG may be used to normalize values within a range which will be focused on an expected range of values e.g., between nearly dead tissue and very dead tissue), rather than a complete range (e.g., between dead tissue and live tissue). This may result in better discrimination ability.

Alternatively to a simple threshold, different degrees of emission (per volume or wall unit) may be translated into different type of the myocardial substrate. For example, in patients with advanced age and disease of the heart there may be progression of spontaneous patchy fibrosis of the myocardium (especially of the atria).

In the presence of patchy fibrosis of the atria the ability to generate and sustain local reentrant circuit is unfortunately enhanced and the ability to transform a propagating wavefront into a fibrillatory propagation of wavelets in much increased.

Optionally, the degree of emission is used to classify a degree of "patchiness" of fibrotic patches. Optionally, identifying (e.g., the location and/or extent) and/or quantifying (e.g., the degree) the amount of patchy fibrosis, for example, using methods described herein may be used for classifying patients according to their propensity to develop and/or sustain atrial and/or ventricular arrhythmias.

In the resulting image, non-active areas are optionally identified as fibrous zones, optionally, if according to the model they are part of the heart wall and not part of non-muscular structures. Optionally, in the image, the wall thicknesses are corrected according to an average wall thickness.

It is noted that some parts of the heart may be reconstructed so that a muscle wall thickness spans only a single voxel.

Various data may be overlaid on the reconstructed image, for example, data from the model or data from other imaging modalities. In particular, electrical measurement data may be overlaid and images of implants may be overlaid.

It is also noted that zones of fibrous tissue may also be identified using other techniques, however, they may have a reduced resolution with respect to the methods described herein. For example voltage mapping using a probing electrophysiologic catheter, who measures the voltage amplitude at each point of contact, may be used.

By associating low voltage with reduced amount of viable tissue one can estimate the presence of fibrous tissue. However, this is an invasive procedure and may be tedious and/or of low accuracy.

It is noted that the imaging techniques described herein may also be used for other organs, such as muscular organs, such as the stomach. In the Example of the liver, fibrosis detection may use lower levels of radioactive tracer and/or image soon after injection, as tracers are often concentrated in the liver and may mask out the non-active parts of the liver. Optionally, such imaging is used to detect liver fibrosis and/or fatty liver.

It is noted that the various normalization and signal analysis methods described herein may also be used when analyzing other measured signals, such as nerve activity signals, for example, whose acquisition is described with reference to FIG. 3B.

Exemplary Reconstruction Method

Figure 3B:
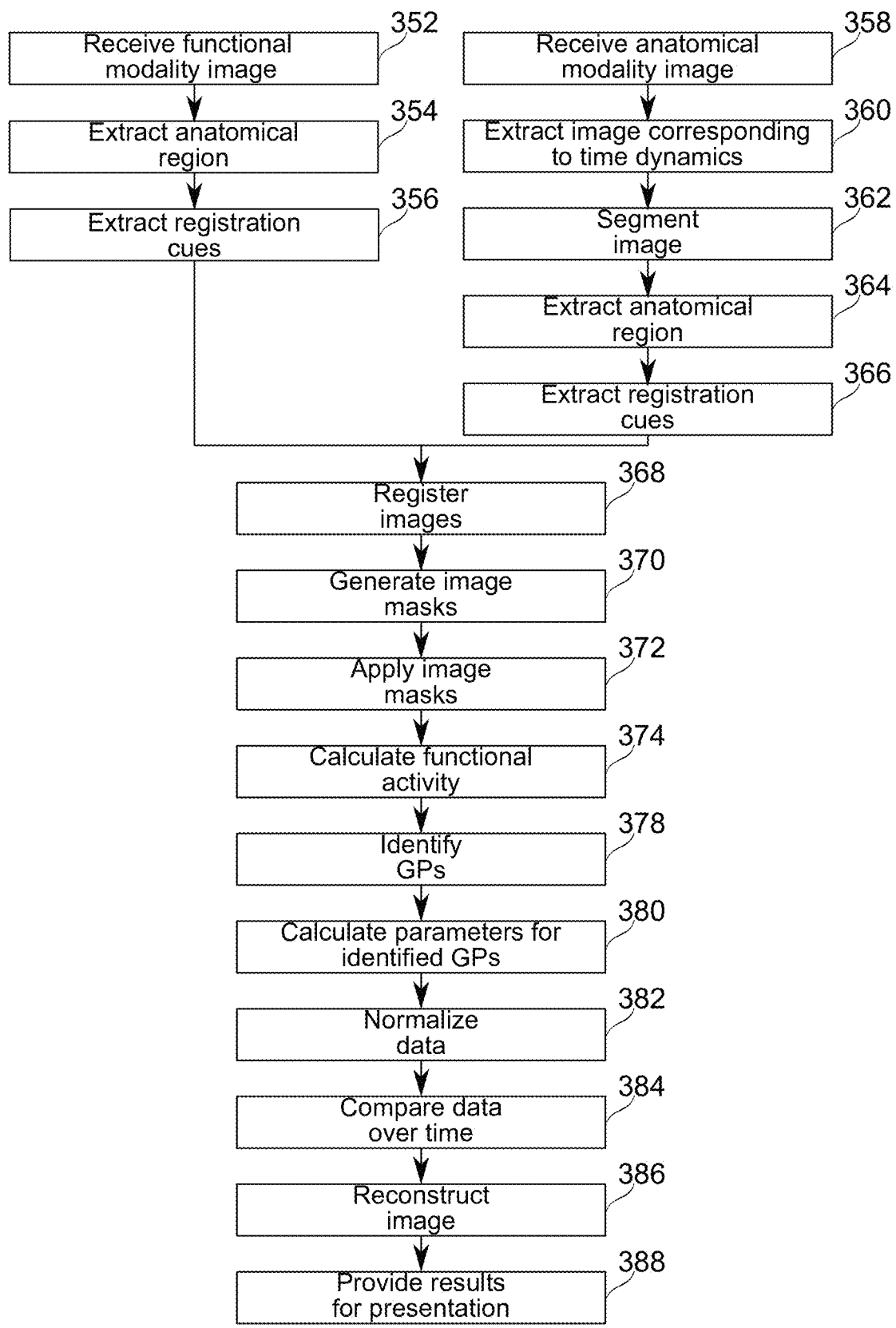
FIG. 3B is a flowchart of a method of radioimaging data processing, in accordance with some exemplary embodiments of the invention.

Reference is now made to FIG. 3B which is a flow chart of a method for processing functional images to identify tissue layers and/or locate one or more ANS components (e.g., ganglions or nerve endings), according to some exemplary embodiments of the invention.

A branch of the flowchart of FIG. 3B begins, and in some embodiments of the invention, at block 352, functional imaging modality data and/or images are received.

The data and/or images comprise, for example, a D-SPECT image and/or other images. Received images, in some embodiments, are of a body part; for example: a torso, abdomen, heart, or another body part, according to the scanning protocol selected. The body part, in some embodiments, includes nervous system tissue to be imaged, and/or the innervated organ itself. For example, nerve tissue comprises GPs (ganglionic plexi) of the heart, intestines and/or another organ.

Optionally, the functional images include regions of activity that denote nerve tissue such as a GP made detectable, for example, by uptake of a radiotracer such as mIBG Viability is optionally measured via the uptake of a muscle metabolic marker, such as Sestamibi.

Optionally, functional data is collected from a body part that has regions where nerve activity is expected, and regions where nerve activity is not expected. For example, during imaging of the heart, data denoting nerve activity is expected from the heart wall and/or surrounding tissues, and no nerve activity is expected from inside the blood-filled hollow chambers. Potentially, noise is received from areas corresponding to the inside of the heart chamber, though no true activity is expected.

Optionally, the noise is removed from the functional data based on the corresponding anatomical image; for example, after image registration. Optionally, intensity denoting noise within blood- or other fluid-filled chambers and/or vessels is removed. For example, intensity readings of the functional data corresponding to heart chambers and/or surrounding blood vessels are removed by applying one or more image mask on functional image. In some embodiments, fluid-filled chamber noise is used in obtaining a noise estimate applicable to other tissue locations.

In some embodiments of the invention, at block 354, an anatomical region is extracted from the image. Optionally, tissue image regions (potentially containing nerve structures) are segmented from hollow spaces (non-innervated, but potentially containing fluid). For example, the wall of the left ventricle (LV) and/or the hollow space within the LV is extracted. Optionally, the extracted region is a layer of tissue, such as the tissue layers forming the LV wall, instead of, for example, the LV including the hollow chamber inside the LV. In exemplary cases of kidney imaging, the walls of the renal artery are extracted and/or the inside of the artery is extracted. When imaging other organs, dominant portions of the organ are optionally selected.

In some embodiments of the invention, at block 356, one or more registration cues are extracted from the image. Potential sources of registration cues include, for example, the organ of interest, and/or surrounding anatomical structures. Particular examples include the LV axis, liver, heart septum, RV, and/or torso. Optionally, registration cues are used to match anatomical images with functional images, and/or to match anatomical images during a physiological cycle, such as the cardiac cycle.

Another branch of the flowchart of FIG. 3B begins, and in some embodiments of the invention, at block 358, anatomical image modality data and/or images are received. Anatomical image modality data comprises data obtained, for example, from a CT, MRI, 3D US, 2D US, or by another modality. The anatomical image denotes the structure of the tissue and/or organ innervated by nerve tissue, such as a GP. The anatomical image denotes the tissue and/or organ structure corresponding to the location of nerve tissue such as a GP. The anatomical images, in some embodiments, contain both the nerve tissue to be functionally imaged and the innervated organ.

Alternatively, anatomical data is received that is not personalized to the patient, for example, from a general anatomical model.

Optionally, anatomical data from an anatomical imaging modality is received to reconstruct an anatomical image of a region of a body of a patient. Optionally, the region comprises a portion of at least one internal body part which borders on a target nerve tissue.

The anatomical images and the functional images denote corresponding regions of the body containing the GPs for identification and/or localization. For example, both modalities are employable to take pictures of the heart, kidney, or other organs. To image GPs of the heart, for example, anatomical and/or functional images of the heart are obtained. To image GPs of the kidney, in another example, anatomical and/or functional images of the kidney, renal artery and/or aorta are obtained.

In some embodiments of the invention, at block 360, images corresponding to different times during a dynamic cycle are optionally extracted and/or acquired. For example, for the heart, images are extracted along the cardiac cycle. Periods selectable along the cardiac cycle for extraction include, for example, the end diastolic volume (EDV) and/or the end systolic volume (ESV). In another example: for the bladder, images are optionally extracted corresponding to a full bladder and an emptying bladder.

In some embodiments, the average image is computed, for example, as (EDV+ESV)/2.

In some embodiments of the invention, at block 362, one or more images are segmented. Segmentation, in some embodiments, is fully automatic. In some embodiments, segmentation requires or potentially involves manual user intervention.

In some embodiments of the invention, at block 364, an anatomical region is extracted. Optionally, the anatomical region corresponds to the anatomical region extracted at block 354. Optionally, the anatomical region is extracted from the segmented image of block 362.

In some embodiments of the invention, at block 366, one or more registration cues are extracted from the image. Potential sources of registration cues include, for example, the organ of interest, and/or surrounding anatomical structures. Particular examples include the LV axis, liver, heart septum, RV, and/or torso.

The branches of the flowchart merge, and in some embodiments of the invention, at block 368, the functional images or data and the anatomical images or data are registered. Optionally, the images are registered based on alignment of the extracted anatomical regions of blocks 354 and 364. Registration is performed manually, automatically and/or semi-automatically.

Optionally, registration takes into account organ dynamics, for example, heart movement. As examples: anatomical images during the dynamic cycle are registered, and/or functional data are corrected for the dynamic movement. As a particular example: intensity readings within the heart chamber are corrected to association with nearby moving heart wall.

In some exemplary embodiments of the invention, at this point, analysis as described herein with respect to identifying scar, fibrotic and/or fibrosis regions in the heart may be applied. Optionally, identification of nerve activity is carried out as well, for example, to detect areas of tissue that lack nervous control, have only practical control or have over control. In an exemplary embodiment of the invention, nerve activity is of interest to assist in determining if a scar is transmural. For example, if there is viable nerve activity at an outer surface of a muscle, this may indicate some viable underlying muscle. Lack of such activity often indicates that the muscle is dead all the way to its outer surface.

In some embodiments of the invention, at block 370, image masks are generated based on the anatomical image and/or data. Optionally, the image masks direct processing and/or visual display of the nerve tissue to specific locations of the image located within the image masks. For example: GPs are displayed and/or processed within the volume of an applied image mask, GPs outside the volume of the image mask are not processed and/or displayed, and/or GPs outside the volume of the image mask are processed and/or displayed differently than those GPs inside the image mask. Optionally or alternatively, masks are used on layers of tissue to indicate viability and/or control thereof.

Optionally, the anatomical images are processed to generate the image mask corresponding to dimensions of at least one internal body part, for example, the walls of the chambers of the heart. For example, a dimension of an internal body part of the specific patient is calculated and used to define the mask.

Optionally, the image masks are selected and/or defined for tissue surrounding a hollow chamber. As examples, image masks are defined based on:

the shape of the heart chamber walls, excluding the hollow region within the chambers;
the arterial wall, excluding the hollow region within the artery; or
the shape of the bladder, excluding the hollow region within the bladder.

It is noted that nerve structures are potentially confined within the tissues defined by the image masks. The hollow spaces (potentially filled with fluid such as blood, urine or other fluids) are expected to be nerve structure free. Optionally, image masks include tissue surrounding the organ of interest.

The image masks are defined, for example, based on:
image segmentation—such as according to the ability of the system to segment the image;
tissue type—such as muscle vs. connective tissue;
organ size;
sub-structures within the organ—such as heart chambers, liver lobes, or kidney parts;
or another method.

Different image masks are optionally generated for different tissue types, and/or for GPs at different locations within the organ. For example, for each of the GPs within the epicardium and myocardium, a respective set of image masks is generated. Optionally, image masks are generated for fat pads.

The image mask comprises, for example, a 2-D surface and/or 3-D volume with shape and/or size selected based on tissues and/or organ parts within the anatomical image. The image mask optionally corresponds to anatomical parts believed to contain the neural tissue for imaging, such as GPs. For example, the mask corresponds to the: walls of the four heart chambers, intestinal wall, bladder wall, renal artery, aortic branch region of the renal artery, kidney, and/or another structure.

In more particular examples, the image mask is generated to contain GPs within the epicardial and/or myocardial tissue of the heart, or kidney innervating GPs at the aorta-renal artery junction.

Optionally, image masks are generated based on an estimated location of the GPs. For example, an estimated location is based on normal patient anatomy, an initial model of the ANS for a patient, and/or known previous ablation or other medical data, such as indications of missing or ablated nervous tissue. Optionally, image masks are generated based on an estimated location of the GPs and dimensions of an internal body part inferred, for example, from an anatomical image. Potentially, this provides an advantage when GPs are not visible on the anatomical image.

Optionally, generated image masks correspond to the segments of the anatomical image. For example, the heart is segmented into chamber walls and the generated image masks correspond to the chamber walls of interest.

In some embodiments of the invention, at block 372, the image masks are applied to the functional image. Alternatively or additionally, the image masks are applied to the functional data. Alternatively or additionally, the image masks are applied to combined functional and anatomical images and/or data, for example, overlaid images.

Optionally, the image masks are applied based on the registration process (block 368). The anatomical information serves as a guide, using the selected image masks, for selective reconstruction of GP related data within the functional image.

The image masks may be correlated with the image to contain anatomical structures having the neural tissues. The application may be based on the image registration, for example, applied based on a common coordinate system. The image masks may be applied to a certain type of tissue containing neural tissue. For example, the image masks may be applied to the epicardium of the heart (e.g., to identify nervous activity on an outer surface of the heart). The image mask may be applied to have its inner surface aligned with the epicardial surface of the chamber wall, such that the image mask contains the epicardial space encompassing the chamber.

Optionally, the generated image mask is correlated with the functional data for guiding the reconstruction of a functional image depicting the target nerve tissue.

In some embodiments of the invention, at block 374, functional activity is calculated within the applied image mask space. Optionally, the average functional activity is calculated. Optionally, the standard deviation of the functional activity is calculated. For the heart example, the functional activity is calculated around each chamber separately, and around the entire heart. Average activity for the chambers may be denoted by A1LV, A1RV, A1LA, and A1RA. Average activity for the heart may be denoted by A1H. Standard deviation of the activity may be denoted by SD1LV, SD1RV, SD1LA, SD1RA, and SD1H. Optionally, average activity and/or standard deviation may be calculated for the entire functional image or data.

Optionally, average activity and/or standard deviation is pre-set, e.g., based on previous imaging of the same patient, based on "normal" patient activity etc.

In some embodiments of the invention, at block 378, GPs are identified within the applied image mask space. It should be noted that the term "GP" is used for ease of discussion, and that the method is optionally applied in some embodiments for identifying ANS component(s) or for extracting or identifying other information relating to neural activities, or other tissues. Alternatively or additionally, GPs are identified within the organ volume and/or nearby tissues. Optionally, GPs identified within multiple different image masks that are combined into a single image of all the identified GPs, for example, the identified GPs within the organ. Alternatively or additionally, GPs identified within corresponding image masks of multiple frames over time are combined—such as all image masks of the LV myocardium during the cardiac cycle.

Optionally, areas of extreme activity are identified. For example, epicardial GPs (EGP) and/or myocardial GPs (MGP) are identified based on extreme mIBG activity. Optionally or alternatively, areas of diffuse activity are identified, indicating areas with nerve endings connected to muscles. Optionally, such areas are assumed to be relative thin (e.g., within 1-3 mm or up to 5 or 7 mm) away from cardiac wall.

Optionally, GPs are identified based on one or more predefined thresholds and/or rules. Optionally, GPs are identified based on size. Alternatively or additionally, GPs are identified based on activity level in reference to average activity and/or surrounding activity. Alternatively or additionally, GPs are identified based on connectivity between GPs.

In some embodiments, the GP is identified as an object within a particular size constraint. The constraint is, for example, at least about 4×4×4 mm, such as for an EGP; or about 2×2×2 mm, such as for an MGP. Alternatively or additionally, the GP is identified by comparing calculated activity (image intensity) of a certain region to surrounding activity in the same image mask. Alternatively or additionally, the GP is identified by comparing calculated activity within the image mask to activity in another image mask. For example, the EGP is identified as satisfying the rule that the total activity of the EGP is a predefined factor times the standard deviation (SD1 and/or SD2), above average activity (A1 and/or A2), and/or the adjacent activity surrounding it is lower than half of the EGP activity. Optionally, activity is corrected for volume. Optionally, the user selects and/or modifies the predefined factor. For example, the MGP is identified as satisfying the rule that the total activity of the MGP is another predefined factor times the standard deviation (SD1 and/or SD2), above average activity (A1 and/or A2), and/or the adjacent activity surrounding it is lower than half of the MGP activity, optionally corrected for volume. Optionally, the user selects and/or modifies the predefined factor.

Optionally, identification of GPs is performed per frame, optionally per frame of the dynamic cycle (e.g., cardiac cycle).

In some embodiments, the identified GP is automatically related to a tissue type. Optionally, the identified GP is related to the tissue type based on the applied image mask. Alternatively or additionally, the identified GP is related to the tissue type based on the characteristics of the intensity readings. For example, large sizes (denoting large GPs) are potentially only to be found in certain tissues. Optionally, different types of GPs are related to different tissues. For example, myocardial GPs are related to the myocardium and/or epicardial GPs are related to the epicardium.

In some embodiments of the invention, at block 380, one or more parameters are calculated for the identified GPs (also referred to herein as GP parameters). Examples of parameters include:

average size;

specific activity—expressed, for example, in counts per voxel and/or GP/average counts in the corresponding image mask volume;

power spectra—for example, the power below 1 Hz, power between 1-5 Hz, and/or a ratio of high to low frequencies;

normalized power spectra;

GP connectivity map—for example, connectivity and interaction between different GPs; and/or number of GPs per predefined area—expressed, for example, as GP density number/cm$^2$.

For identified EGP, one or more of following parameters is calculated in some embodiments: EGP size, EGP specific activity, EPG power spectra graph, EGP normalized power spectra, and/or a map of EGP connectivity. EGP normalized power spectra are calculated, in some embodiments, as the difference between the EGP power at different frequencies minus the power of the total counts from the myocardial image mask space.

Optionally, calculation of GP parameters is performed per frame, optionally per frame of the dynamic cycle (e.g., cardiac cycle).

In some embodiments of the invention, at block 382, the calculated and/or other parameters are normalized. Normalization optionally take place at one or more blocks of the method, for example, during and/or after acquiring the functional and/or anatomical images, upon calculation of functional activity, upon identification of GPs, upon calculating parameters for the GP, upon comparison of data over time, or at other blocks.

Examples of normalization techniques (e.g., which may also be used for normalizing metabolic activity to detect fibrosis) include:

raw data;

raw data divided by the raw data value in a known fixed anatomical location acquired at roughly the same time, for example, the activity of the tracer in the patient's mediastinum;

normalization to a normal patient data set;

normalization to a value of the activity at the first or the last image acquisition from a sequence of acquisitions;

normalization to value acquired in different physiological states such as rest/stress;

a combination of some or all of the above; and/or other methods.

Alternatively, normalization is performed instead of and/or in addition to the normalization of block 382 before a different block in the process. For example, normalization is optionally applied before GPs are identified in block 378.

Normalization potentially assists identifying the GPs. For example, activity at a local region, such as mIBG activity, is compared to an average value and/or standard deviation across the organ volume, within the image mask space and/or relative to a predefined threshold.

Alternatively or additionally, the calculated data (e.g., blocks 374, 378, 380) and/or measured functional intensity are corrected for sensitivity. Optionally, sensitivity correction is performed within each image mask and/or in related image masks. For example, different areas potentially have relatively higher or lower sensitivity to uptake of the radioagent. Optionally, the anatomical data is correlated to the sensitivity. Optionally, the image masks are generated (block 370) based on different sensitivity levels; for example: one set of image masks for higher sensitivity nerve structures, and another set of image masks for lower sensitivity nerve structures.

Optionally, the different sensitivities are normalized to a common baseline.

Alternatively or additionally, measurements of the functional data are normalized. For example, measurements of uptake of the radioagent are normalized to the level of corresponding chemical in the patient. Optionally, intensity measurements are normalized according to the level of activity of GP being identified. Optionally, measurements denoting activity of the GPs are taken. For example, in the case of mIBG, measurements are optionally normalized to the level of norepinephrine (NE), adrenaline and/or epinephrine in the patient. Optionally, the level of NE is measured in the blood, urine, or other body fluids. Intensity of mIBG uptake is normalized based on the measured NE.

Additionally or alternatively, mIBG measurements are normalized to a decay function, such as decay over time since injection of mIBG In another example, the level of activity is measured by non-chemical methods. For example, normalization of mIBG is performed based on measurements taken during a cardiac stress test.

Measurements comprise, for example, ECG measurements, heart rate, cardiac output, and/or other measurements. Optionally, measurements are correlated with levels of activity of the GPs being identified, for example by a table, mathematical equation, or other method.

In some embodiments of the invention, at block 384, data is compared over time. Optionally, changes in GP parameters over time are identified. Optionally, dynamic changes of the calculated parameters between different acquisition times are determined. For example, the changes in GP activity over time are calculated, from injection till 6 hours post injection, by repeating the image acquisition several times during this time window. The functional images are optionally acquired at more than one time after the tracer injection.

In some embodiments of the invention, at block 386, a functional image is reconstructed based on the mask applied to the functional data and/or image.

Alternatively or additionally, an image is reconstructed based on the mask applied to the combined functional and anatomical data and/or images. The reconstructed image potentially contains the identified GPs, for example, as regions of increased intensity. The reconstructed image is optionally overlaid on the anatomical image, illustrating the physical location of the GPs.

Alternatively or additionally, the characteristics of the GPs within the functional image are reconstructed. The reconstruction is instructed by the image mask.

In some embodiments of the invention, at block 388, the calculated results from, for example, block 378, 380, 382 and/or 384, and/or reconstructed images (block 386) are provided for presentation or otherwise provided to the operator. They are, for example, presented on a monitor to a physician. Additionally or alternatively, the calculated results and/or reconstructed images are stored in a memory for future use, such as diagnosis. The calculated results potentially assist in diagnosing the patient and/or in guiding treatment.

Optionally, the results are provided for presentation on a certain frame, for example, the end systolic frame. Alternatively, results are provided for presentation on multiple frames, for example, a video of the cardiac cycle.

In some embodiments, the reconstructed functional image or combined functional and anatomical image is provided for registration during a treatment procedure. Optionally, the reconstructed functional image is overlaid on and/or registered with anatomical images obtained during the treatment procedure. Overlaid and/or registered images are optionally used by the operator to physically determine locations of the GPs during the treatment.

The method of FIG. 3B has been described with reference to the heart. The method is not limited to the heart, and is used in some embodiments for other organs, including hollow fluid filled organs such as stomach, aorta, or bladder; and/or solid organs such as kidney or liver. GPs and/or nerve endings are identifiable in these other organs in some embodiments. For example, the aorta is segmented based on surrounding structure such as bones, muscles, and/or branching arteries; and image masks generated accordingly. The liver, in an exemplary embodiment, is segmented based on anatomical liver lobe divisions.

Ablation Assessment and/or Correction

Various techniques may utilize the image of fibrous zones. Some examples are described below.

Figure 4:
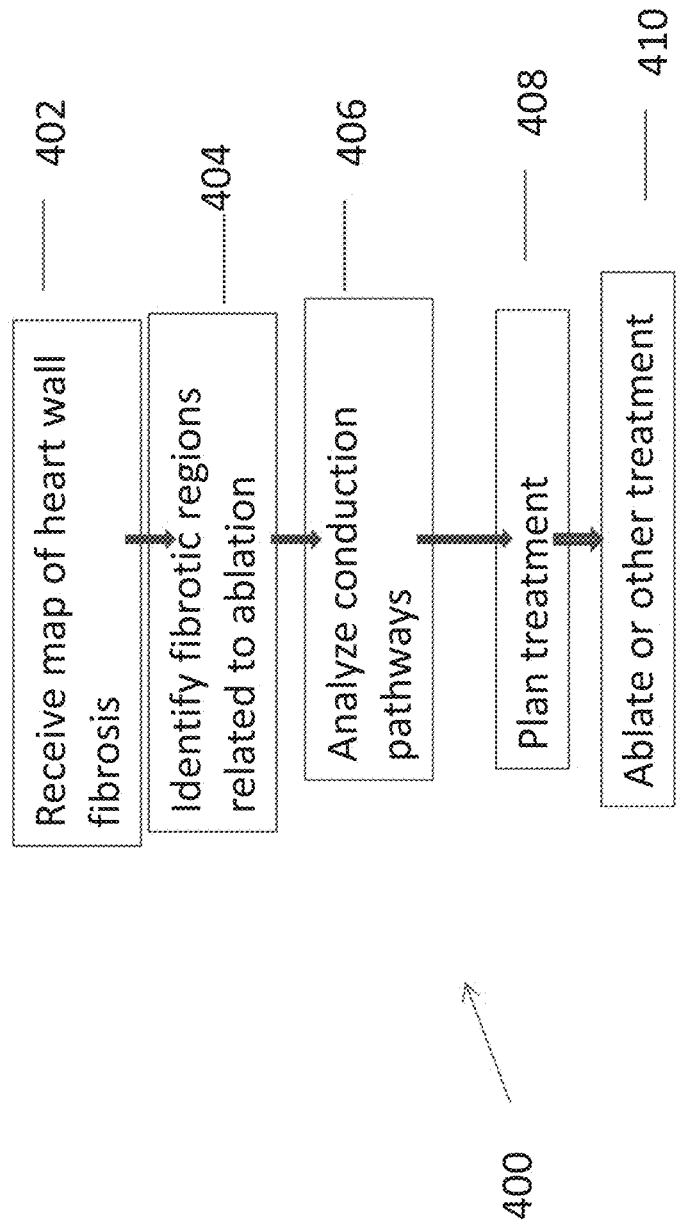
FIG. 4 is a flowchart of a method of ablation assessment and/or correction, in accordance with some exemplary embodiment of the invention.

FIG. 4 is a flowchart 400 of a method of ablation assessment and/or correction, in accordance with some exemplary embodiment of the invention. In some embodiments, ablation assessment and/or correction may be determined based on an image including map of fibrous and non-fibrous zones in an organ to be treated, e.g., a heart. While fibrous zones may be the result of a disease, developmental problem or infarct, a common cause of fibrous zones in the heart is scarring caused by intentional ablation. In some exemplary embodiments of the invention, the reconstructed image is used to assist in reconstructing the effect of previous ablations and/or plan future ablations and/or other modifications to conduction pathways in the heart. Specifically, it may be of interest to identify gaps where ablation was planned but was not successfully carried out, as indicated by the zone image (e.g., an image including map of fibrous and non-fibrous zones) and/or by a combination of the zone image and other data such as electrophysiology measurements in the heart.

At 402 a map of the fibrous zones in at least a portion of a heart wall is provided. For example, the map may be displayed to an operator or provided in a non-transitory data storage medium.

At 404 zones related to ablation are optionally identified and/or localized. This step may be manual or automatic, for example, using template matching. In some exemplary embodiments of the invention, the medical history of the patient is used to determine what shape sand/or sizes of ablated zones are expected and such zones are identified in the image. In another example, an expert indicates such zones.

At 406, the available conduction pathways in the heart are identified.

Optionally, this identification includes identifying gaps such as gap 210 (FIG. 2A) and pathways such as pathway 212 (FIG. 2A) and 252 (FIG. 2C). Such identification may also take into account "natural" fibrous zones.

At 408, treatment is optionally planned (e.g., to ablate a gap), for example, according to the discovery of undesirable pathways in the heart. In other cases, pharmaceutical treatment may be decided, for example, based on lack of gaps and/or other patterns of zones. In some exemplary embodiments of the invention, patient symptoms (e.g., recurring arrhythmia) are used together with the fibrous zone map to select treatment.

In some embodiments, the location of fibrous zones are used to set parameter for treatments, for example, to indicate a needed and/or allowed size and/or shape of ablator, to select a location for pacing during a procedure or after a procedure and/or to identify locations where ablation may cause perforation.

Figure 6A:
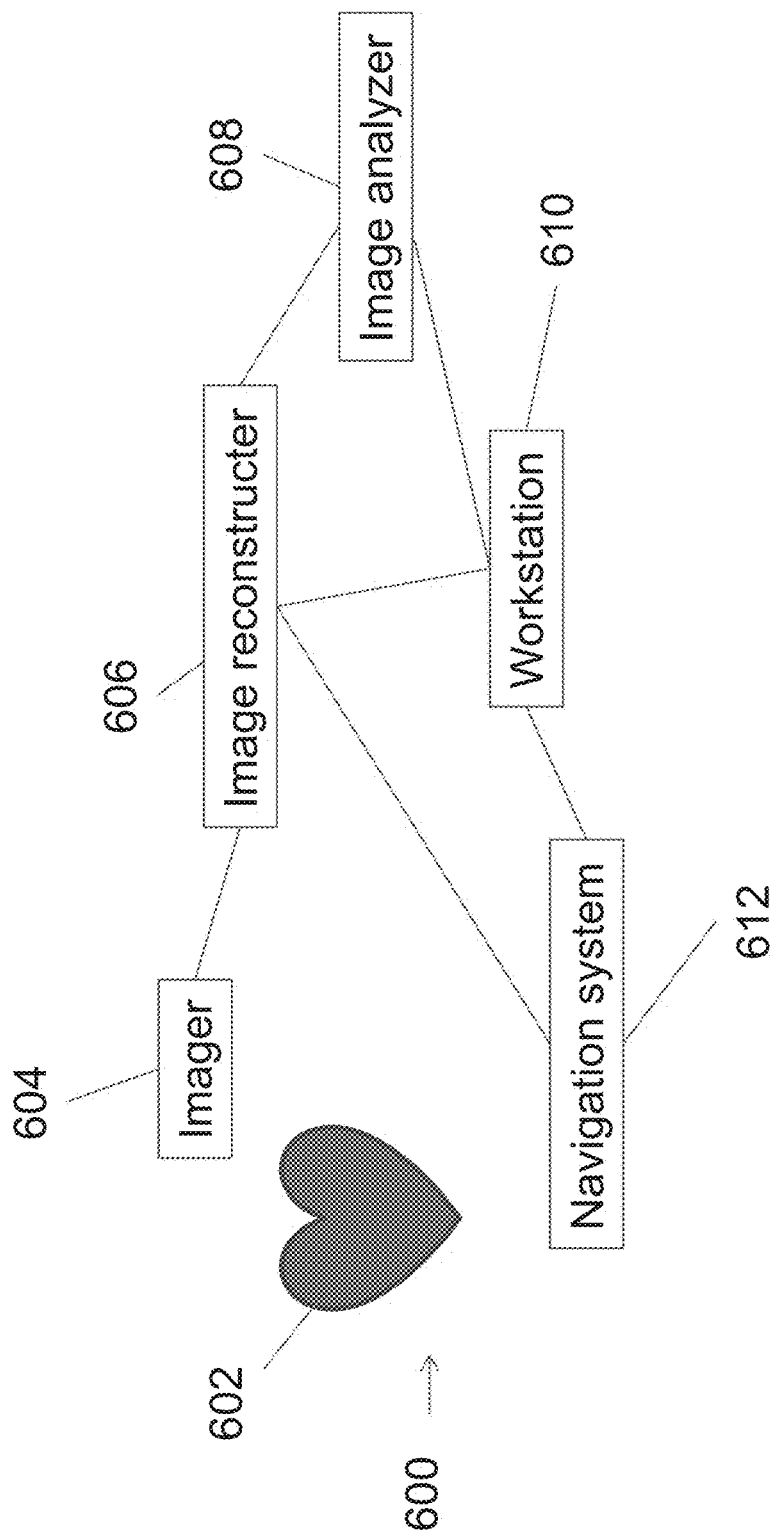
FIG. 6A is a schematic showing of a system for imaging the heart, in accordance with some exemplary embodiments of the invention.
Figure 6B:
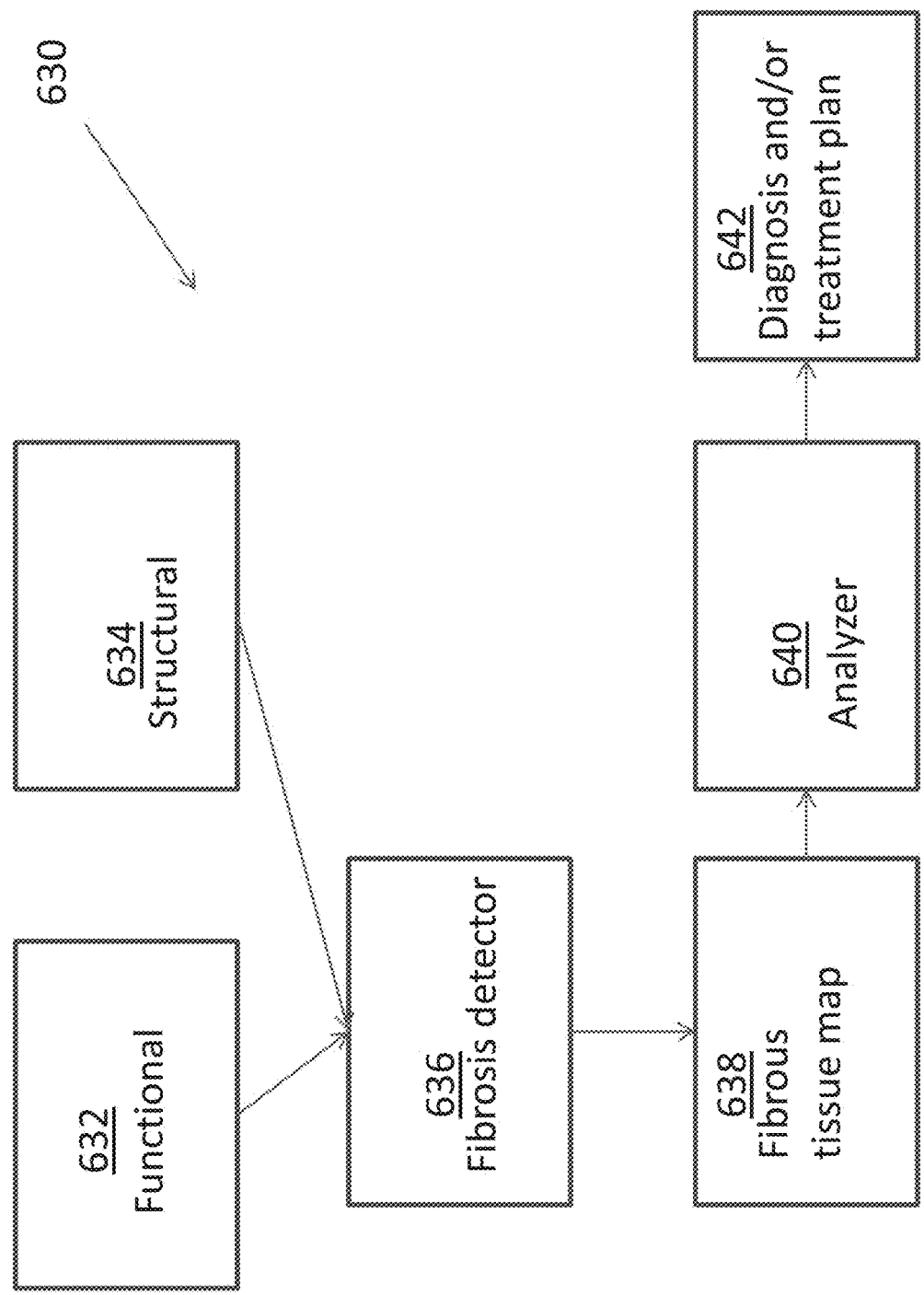
FIG. 6B is a schematic showing of a system for image analysis, in accordance with some exemplary embodiments of the invention.

At 410, such treatment is optionally carried out, optionally using real-time guiding of where fibrous zones are located (e.g., FIGS. 6A-B).

Exemplary Risk Assessment, Diagnosis and/or Planning

Figure 5:
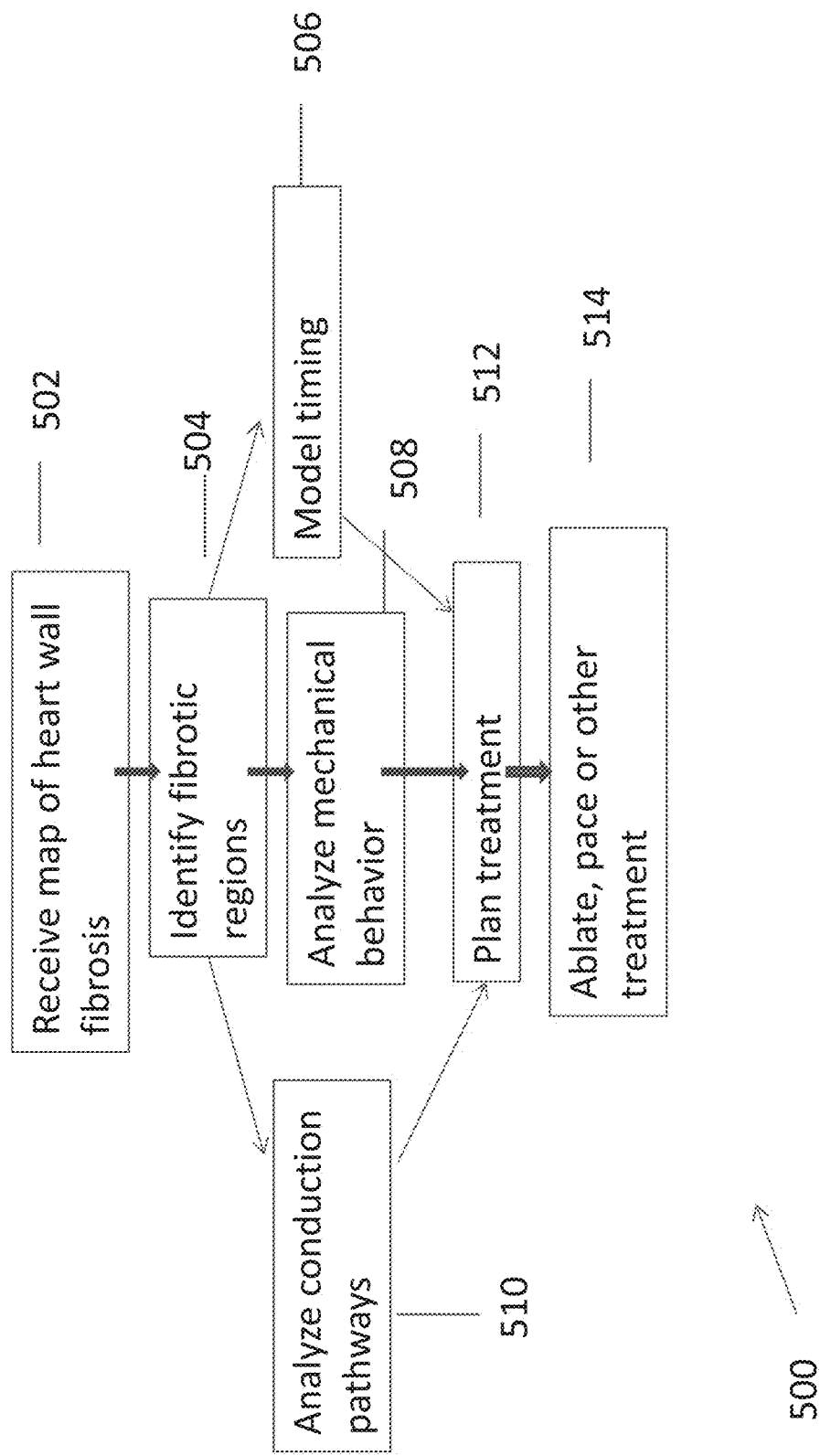
FIG. 5 is a flowchart of a method of assessing risk, in accordance with some exemplary embodiments of the invention.

FIG. 5 is a flowchart 500 of a method of assessing risk and/or diagnose and/or plan therapy, in accordance with an exemplary embodiment of the invention.

At 502, a map of the fibrous zones in at least a portion of a heart wall is provided.

At 504, fibrous zones are optionally identified, for example, using the methods as in 404 (FIG. 4). In some exemplary embodiments of the invention, also "natural" zones are identified.

Various analyses may be applied. For example, at 506, the timing of contraction of different parts of the heart may be determined, for example, to assess changes in conduction patterns which increase (or decrease) cardiac output and/or change a risk of aneurism.

For example at 508, mechanical behavior of the heart may be analyzed. For example, fibrous zones do not apply and/or apply less contraction force and/or at different times than nearby tissue and may be ballooned by increased pressure in the heart.

For example, at 510, conduction pathways may be analyzed. Such analysis can include, for example, an estimation of AF risk (e.g., based on size, shape and/or pattern of fibrous zones in an atria). In another example, an estimation of ventricular arrhythmia (e.g., VT) risk is provided, for example, by identifying long conduction pathways (e.g., between and around fibrous zones). Such analysis may also take into account EP data, for example, which indicates areas with ischemia and/or areas with reduced conduction velocity.

At 512, treatment is optionally planned. Optionally, the treatment is not for a risk assessed in 506-510. For example, identification of fibrous zones can be used to select an optimal place for a pacemaker lead.

In some embodiments, the analysis of the image is used to interpret EP measurements and/or mechanical measurements (e.g., contraction amount, speed, force and/or change in thickness). For example, a low signal may have different meanings if acquired at a fibrous zone or away from a fibrous zone. In addition, the identification of an intra-muscular fibrous zone can assist in interpreting electrical measurements which are associated with weaker than expected mechanical activity.

In some embodiments, fibrous zones are used to assess the usefulness of inserting a stent or performing PCTA or other vessel modification.

In some embodiments, fibrous zones are used to assess the usefulness of gene therapy or other treatment designed to convert fibrous tissue to non-fibrous tissue or healing weak tissue (which generally cannot be done for fibrous tissue).

In some embodiments, fibrous zones are used to diagnose a mechanical condition such as HOCM or various cardiomyopathies, such as dilated cardiomyopathies.

In some embodiments, fibrous zones are used to assess a risk of cardiac dysfunction due to ischemia or a further infarct and/or assess a prognosis for a patient with heart failure.

It is noted that identification of fibrous zones, optionally together with information such as viability of tissue, electrical behavior and/or blood flow may be used to diagnose conditions otherwise diagnosed only using biopsy, sometimes after death.

At 514, the heart is optionally treated, for example, by ablation, by vascular manipulation (e.g., stent implantation), heart reshaping apparatus implantation, valve implantation electrical stimulation, surgery and/or pharmaceuticals.

Some Examples of Diagnosis and Treatment

In one example, a heart is imaged in a multiplexed mode (e g, mIBG and MIBI), for example, to detect areas of scar of the heart muscle, some of which are transmural (extending from the endocardium to the epicardium) some of which are non transmural. In an exemplary embodiment of the invention, data is acquired when the patient was injected with two different radiotracers (e.g., simultaneous dual tracer imaging): one detecting the viability of the myocardium and the other detecting the innervation of that myocardium. By looking at the results of this imaging it is possible to identify areas that are viable but partially innervated or denervated, both in proximity to an area of a scar. It was discovered that minute alteration of the autonomic tone can induce an improper, sustainable state of impulse propagation, similar to that seen during cardiac arrhythmia. Two mechanisms for arrhythmia therefore appear, one due to fibrosis tissue being pro-arrhythmic and one due to the effect of changes in autonomous nerve activity on such tissue. It is believed that the adjacent location of innervated to denervated area (causing spatial dispersion of electrical properties during altered state of ANS activity) interacts with the presence of a structural scar (e.g., caused by disease, ablation or be natural such as a valve) can act to transform part of the pathology created by the anisotropy to a sustained arrhythmia.

In an exemplary embodiment of the invention, the size and/or shape and/or degree of fibrotic tissue near scar tissue is used to assess risk of arrhythmia and/or select treatment to reduce such tissue. Optionally, electrical measurements are taken during various levels of nervous activity to see if the above mechanism of arrhythmia is caused. Optionally or alternatively, electrical measurements in a fibrosis area are used to detect near-arrhythmic states, where a signal propagates out of turn (and sync with nearby healthy tissue) but does not sustain.

In an exemplary embodiment of the invention, the pattern of fibrotic and fibrosis tissue is used to select treatment. For example, the pattern can indicate the degree and/or possibility of treating an arrhythmia by ablation or by drugs. Optionally, a simulation is run to determine the possible effects of drugs and/or ablation on an arrhythmia, based on a model of propagation which uses the fibrosis and scar tissue detected and/or which uses an expected effect of change in conduction velocity due to nervous control or lack thereof. In an exemplary embodiment of the invention, the simulation is a FEA model (or other spatial numerical method) of the heart using, for example, fibrosis information, conduction velocity and/or other electrical data and/or anatomical models of the heart.

In one example, detection of channels with fibrosis (e.g., as in FIG. 2D) suggest selecting a dosage of medication suitable to increase refractory period by enough to prevent there being tissue to sustain an arrhythmia. In another example, conduction velocity is reduced (e.g., by 50%) to an amount sufficient to prevent arrhythmia, based on the simulation. Optionally, such simulation (e.g., to test expected effects of medication and/or exercise) is provided at a server and accessible, for example, during imaging, at a doctor visit and/or at a telemedicine service center.

In some exemplary embodiments of the invention, an electrical mapping system is used together with the imaging. In one embodiment of the invention, electrical sensing is carried out to verify the existence of channels of fibrosis tissue. In another example, such a system is used to ablate fibrosis tissue to treat arrhythmia.

In some exemplary embodiments of the invention, identifying of fibrotic tissue and/or of denervated tissue is used to guide data acquisition using such a mapping system. For example, such identifying may indicate locations suspected of acting as pro-arrhythmic conduction channels or areas which under certain condition cause or sustain arrhythmias. Mapping may be focused on areas identified as problematic based on fibrosis and/or denervation.

In an exemplary embodiment of the invention, identifying of fibrosis tissue is used to guide ablation. Optionally, ablation is selected so as to not maintain areas of fibrosis of a certain size, shape and/or capability of sustaining a re-entrant circuit. In one example, fibrosis areas are ablated to not have a width greater than a certain size, such as 3, 5, 10, 15 or an intermediate size in mm Optionally or alternatively, the maximum circuit length in the area is limited, for example, based on expected conduction velocity. Optionally, the disallowed circuit length is greater than that of a simple closed circle, reflecting that such a circuit may be convoluted. For example, a circuit is assumed to be up to 2, 3, 4 or smaller or intermediate factors of the length of the area perimeter. In another example, fibrosis areas are ablated to ensure they are not large enough for reentry circuits (or suitable drugs given to make them effectively too small). In another example, fibrosis areas are ablated so as not to include "fjords" or other peninsula-like shapes which may serve as a source or arrhythmia. This may be reflected in ablating to reduce area width or such peninsula may be ablated so they become islands.

Exemplary Imaging System

FIG. 6A is a schematic showing of a system 600 for imaging a heart 602, in accordance with some exemplary embodiments of the invention. It is noted that one or more or parts of the components may be provided at a remote location, for example, using a server with remote access.

An imager 604, for example a functional modality, e.g., SPECT or D-SPECT device as described above is used to acquire information (e.g., nuclear medicine information) about the heart. Optionally, the imager also acquires a structural image to provide a model for the reconstructions. Optionally or alternatively, imager 604 also collects cardiac phase information and/or respiratory phase information. It is noted that such information may also be reconstructed from the acquired data, in some embodiments of the invention.

An image reconstructer 606, optionally bundled with imager 604, but alternatively provided at a remote location, may be used to reconstruct the fibrous-zone showing image, for example, as described above. Optionally, reconstructer 606 includes storage within which is stored a model used for the reconstruction, for example, as described herein.

An image analyzer 608 optionally bundled with one or both of imager 604 and image reconstructer 606 is optionally provided and used to perform automatic and/or semi-automatic analysis of the image, for example, to identify the different types of fibrous zones. Communication between parts of the system may be, for example, by wired means, by wireless means and/or using portable storage devices, such as flash memory devices.

Optionally, reconstructer 606 and/or analyzer 308 are programmed to apply one or more of the methods described in FIGS. 3A-3B or elsewhere in this specification.

Optionally, a work station 610 is used to control one or more of imager 604, reconstructer 606 and analyzer 608 and/or to display results generated thereby.

In some exemplary embodiments of the invention, a navigational system 612 is provided which is optionally controlled by work station 610 and which may be loaded with targeting and/or map information provided by the image. In one example, the navigational system comprises a catheter with a position sensor (e.g., the Biosense Webster Carto® system) and the image is used to guide a procedure performed using the catheter. Such a navigation system may be used with other CathLab equipment such as an X-ray machine. Fibrous zones are optionally overlaid on an image acquired by the x-ray machine. Optionally, registration is provided manually or using the above mentioned position sensor.

In an exemplary embodiment of the invention, the fibrous zone is used for safety, for example, to indicate to a user that he is about to ablate a fibrous area, rather than live tissue or to warn of ablation parameters risk causing perforation of tissue.

Optionally or alternatively, when temporary pacing, the system can indicate that pacing is being provided at a fibrous zone or at a location where fibrous zones interfere with the desired effect of the pacing.

In an exemplary embodiment of the invention, an ablation catheter is provided with a radiation detector, e.g., at a tip thereof. Such a detector may be used to determine if the catheter is adjacent a fibrous zone, as such a position may result in a smaller amount of radiation (if a suitable tracer is provided in the patient), for example, as compared to an average amount detected from the wall. Optionally, such a detector is collimated, for example, using a fan beam collimator which is focused at a location a few mm from the catheter (e.g., where the heart wall is expected to be).

Optionally or alternatively, the catheter uses a map of radiation to determine an expected amount of radiation. Optionally or alternatively, the navigation system uses a map indicating where there is a fibrous zone and where there is viable tissue.

Exemplary Image Analysis System

FIG. 6B is a schematic showing of a system 630 for image analysis, in accordance with some exemplary embodiments of the invention. As shown, a single system is provided, however, separate systems for image construction and for map analysis may be provided as well.

A functional image 632 (e.g., NM, from an NM imager or data store) and a structural image 634 (e.g., a CT image) are combined by a fibrosis detector 636, for example using the methods described above. In an exemplary embodiment of the invention, fibrosis detector 636 uses the structures of structural image 634 to limit the reconstruction of functional image/data 632, and reconstruct multiple sufficient resolution to indicate tissue viability. In an exemplary embodiment of the invention, fibrosis detector 636 normalizes the image to generate a fibrosis map 638, for example, as described herein.

An analyzer 640 (optionally in a different system) receives fibrosis map 638 and generates one or more of a diagnosis, a treatment plan and/or instructions for further diagnosis based on, for example, size and/or shape of the fibrotic areas and/or based on additional information, such as EP information. Optionally, analyzer 640 is integrated into or linked to a treatment and/or diagnosis system, such as Carto® or other system using a position sensor for an EP catheter. Optionally, this allows electrical data collected by the catheter to be integrated without sending it to analyzer 640 (an alternative), and/or indicate desirable treatment options. It is noted that as the heart is complex, treatment plans 642 may have the form of suggested locations and/or alternatives for treatment.

Examples of Fibrotic Tissue Detection

Figures 7A, 7B:
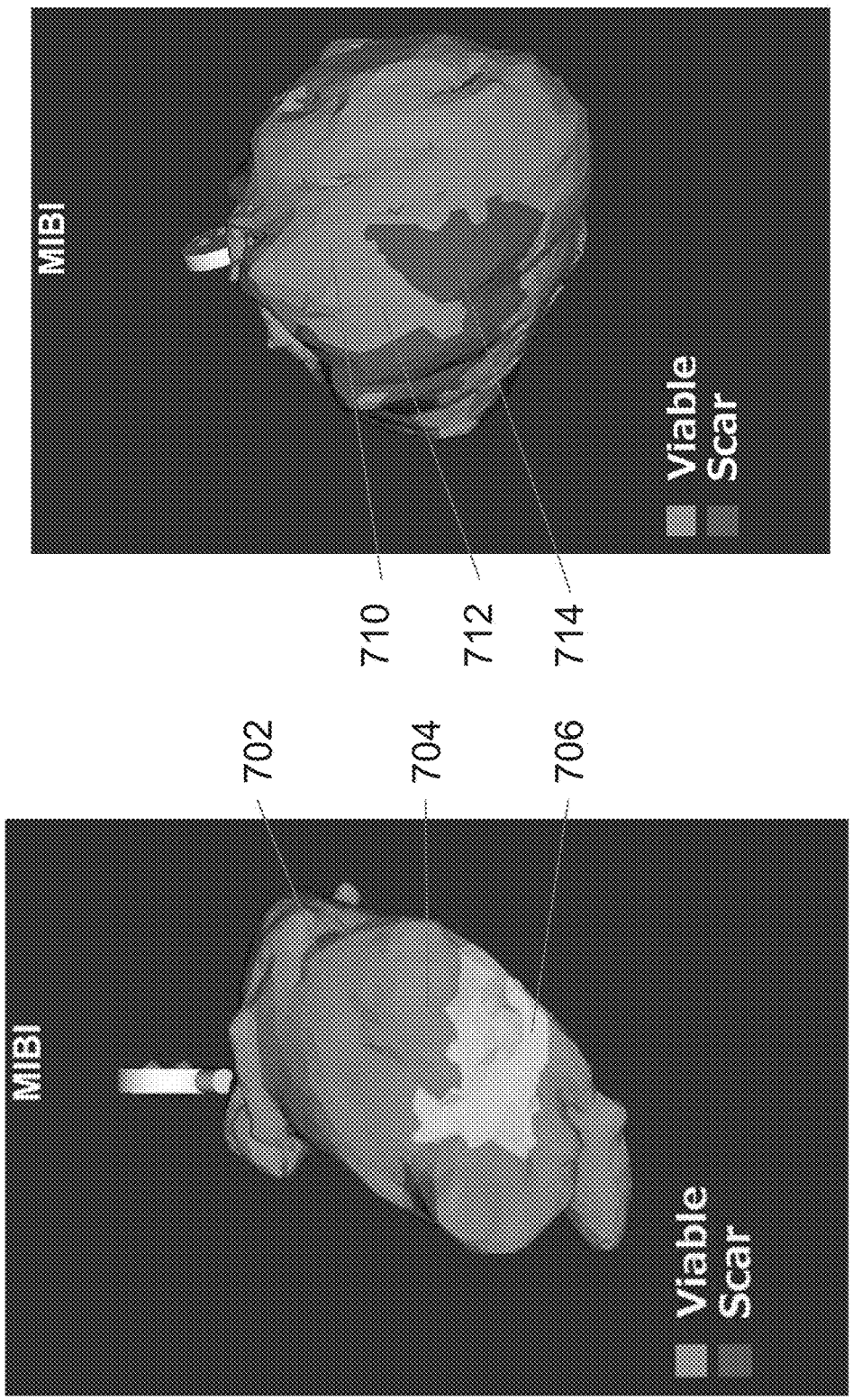
FIGS. 7A and 7B show results of a detection of fibrous zones in a right atrium and a left ventricle respectively, in accordance with an exemplary embodiment of the invention.

FIGS. 7A and 7B shows results of a detection of fibrous zones in a left atrium and a left ventricle respectively, in accordance with an exemplary embodiment of the invention.

FIG. 7A shows a right atrium 702 having healthy muscle tissue 704 and a fibrous zone 706. It is noted that this zone is in yellow, as the tissue is not totally dead, rather it includes a mixture of scar tissue and viable muscle tissue. In this case it appears to be the result of a repeated ablation of the right atria in the attempt to form a line of ablation to treat atrial fibrillation. That the attempt failed can be seen in the figure. It is suggested that there do not currently alternative exist non-invasive methods of assessing the results of ablation.

FIG. 7B shows the left ventricle 710 of a patient with ventricular arrhythmia, probably due to an infarct. Viable tissue 712 is shown near scar/fibrotic tissue 714.

Figure 7C:
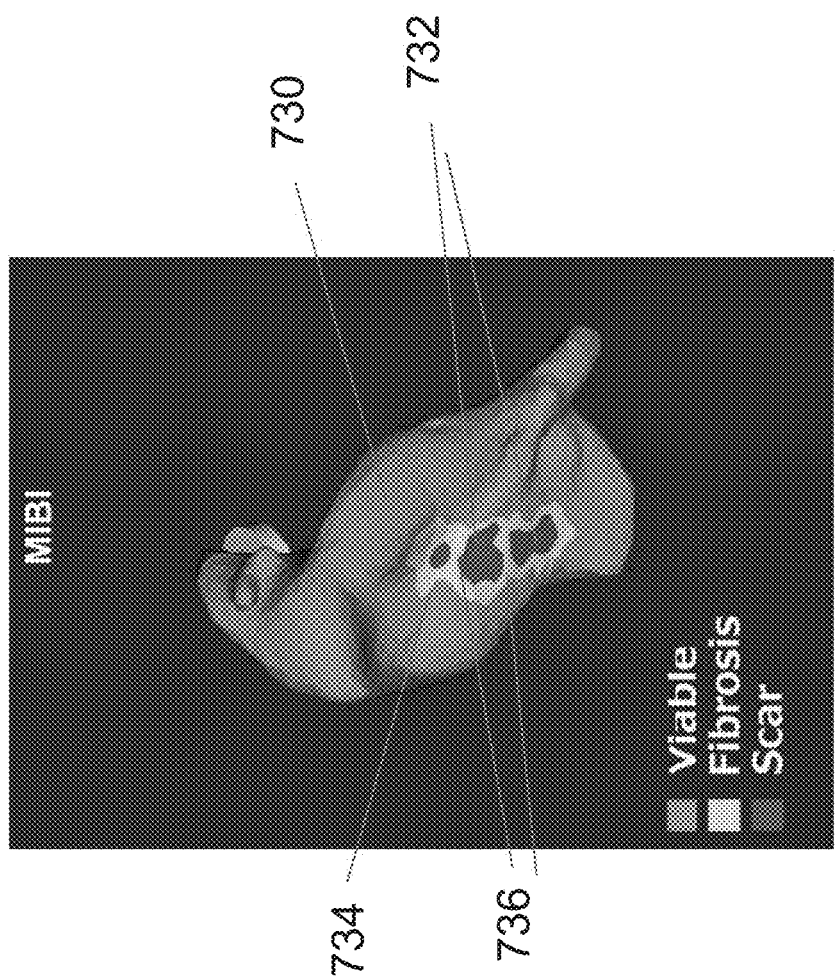
FIG. 7C shows a gap in an ablation line in an atria, detected using methods in accordance with an exemplary embodiment of the invention.

FIG. 7C shows a gap in an ablation line in a right atria, detected using methods in accordance with an exemplary embodiment of the invention.

Reference 730 indicates healthy tissue of the atria. Fully ablated regions 732 (in red) are fibrous. However, there are also regions 734 (in yellow) with only partial ablation and including mixed fibrous and viable tissue.

Possibly more important pathologically are the channels/gaps 736 of viable (conducting) tissue formed between the regions of ablated tissue 732.

This figure highlights the importance of imaging the effects of ablation.

Specifically, while a line of ablation was planned and executed, problems in execution have left conduction gaps 736 which breach the line and may prevent it's functioning and/or be a cause of arrhythmia themselves.

In an exemplary embodiment of the invention, such a patient will be treated by ablating gaps 736 so that ablated area (line) 732 is contiguous.

Optionally or alternatively, conduction and/or lack thereof in gaps 736 is verified using electrical measurements (e.g., a Carto system).

Figure 7D:
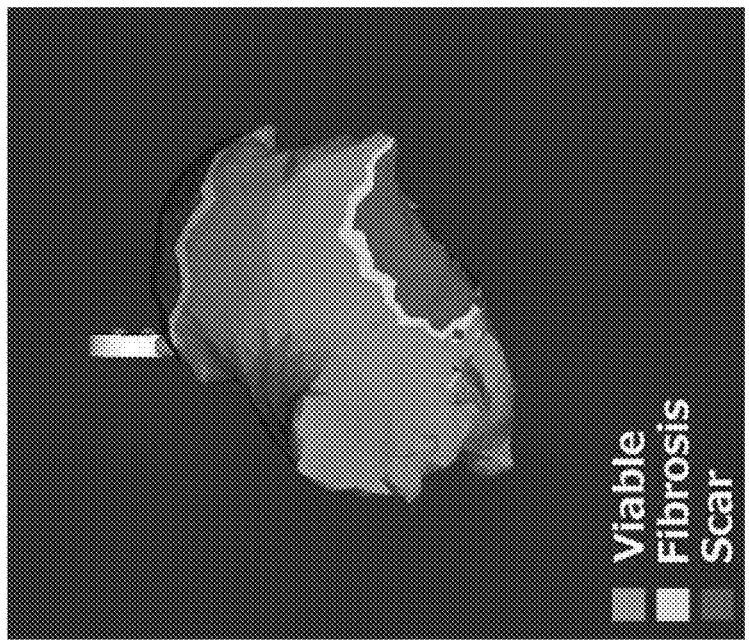
FIG. 7D shows another example of an NM image of a RA with isthmus ablation, identified in accordance with some exemplary embodiments of the invention.
Figure 7D:
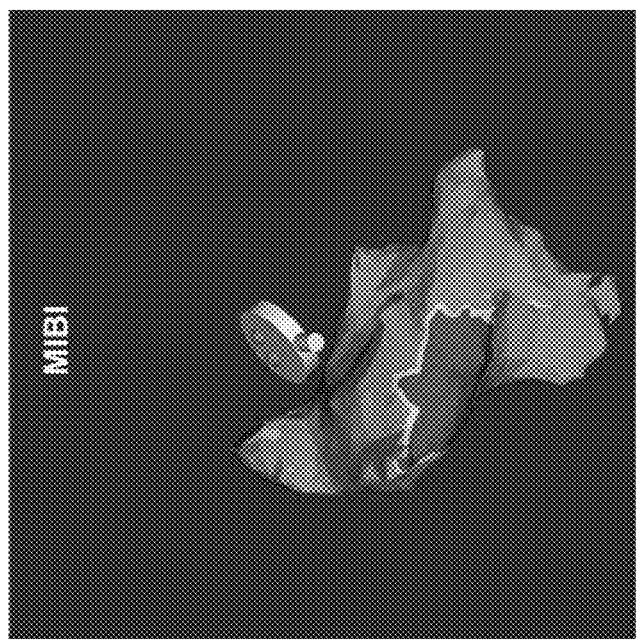
Figure 8:
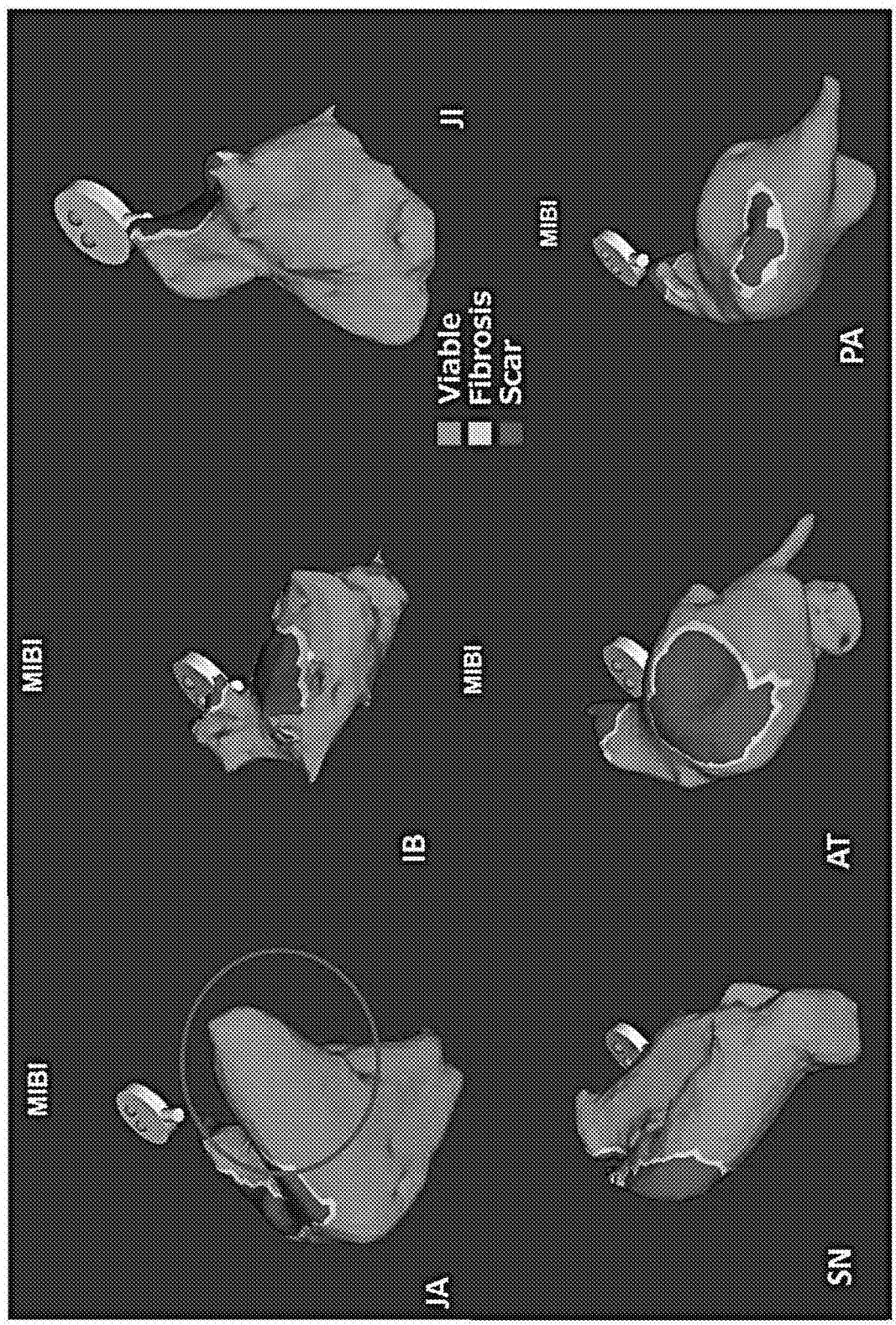
FIG. 8 shows NM images of six examples of RA with fibrosis caused by infarct, identified in accordance with some exemplary embodiments of the invention.
Figure 9:
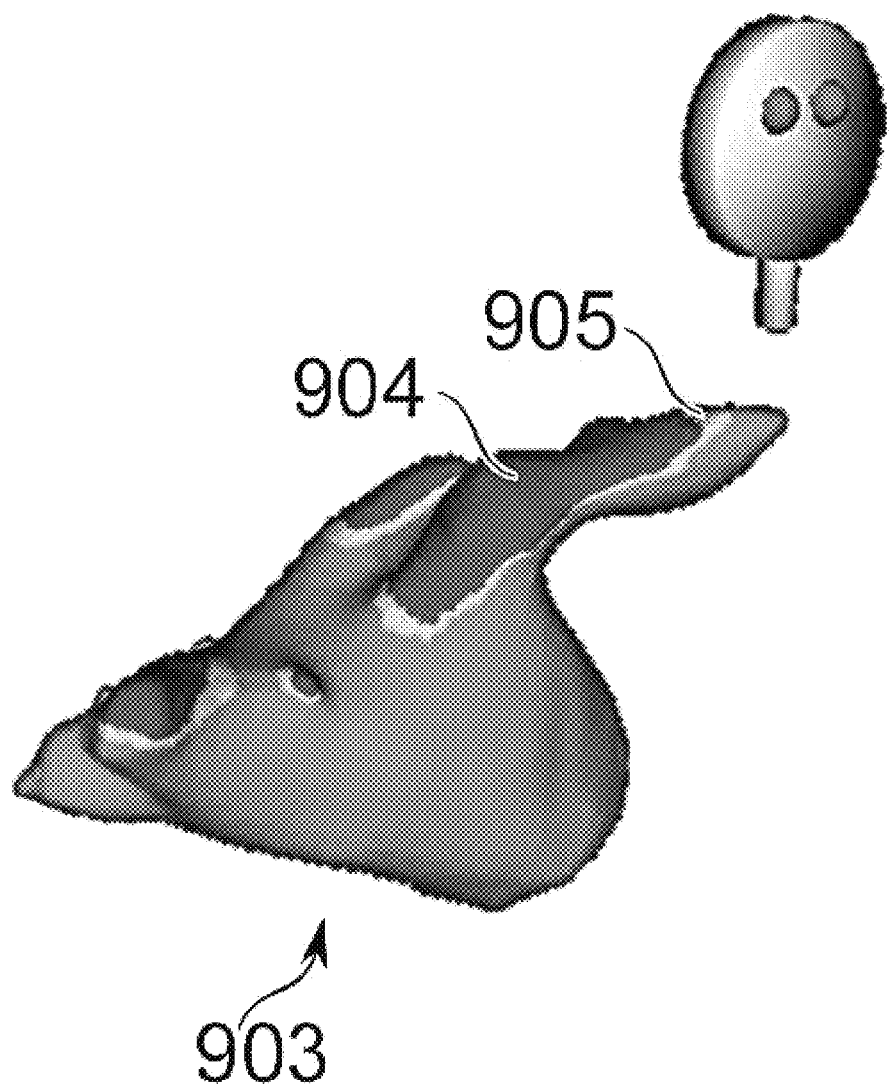
FIG. 9 shows an NM image of left atrium tissue zones with scarring identified, according to some exemplary embodiments of the invention.

FIG. 7C and also FIG. 7D show examples where fibrotic areas are caused by ablation (of the isthmus) (in FIG. 7C, it is believed to be atrial flutter ablations, in FIG. 7D a single atrial flutter ablation). FIG. 8 shows examples where fibrosis is not caused by ablation, but rather by disease.

In an exemplary embodiment of the invention, images (e.g., FIGS. 7C, 7D, 8) are analyzed to determine if a particular fibrosis location is caused by disease or by ablation. Optionally, if caused by disease the morphology is expected to be different and thus treatment may be different.

In an exemplary embodiment of the invention, a lesion caused by ablation is identified based on its having multiple focal areas. Optionally or alternatively, different ablation methods leave different shapes of fibrosis area surrounding scar tissue. Optionally or alternatively, ablation is often a different shape (e.g., lines or relatively symmetric points) from natural damage (which may follow vascular beds). It is noted that ablation often has a characteristic shape with respect to the tissue thickness (e.g., ablation region is larger near the inner surface of the heart), while disease may present different shapes, for example, a larger dead region at the surface or at the middle of wall thickness.

Figure 10:
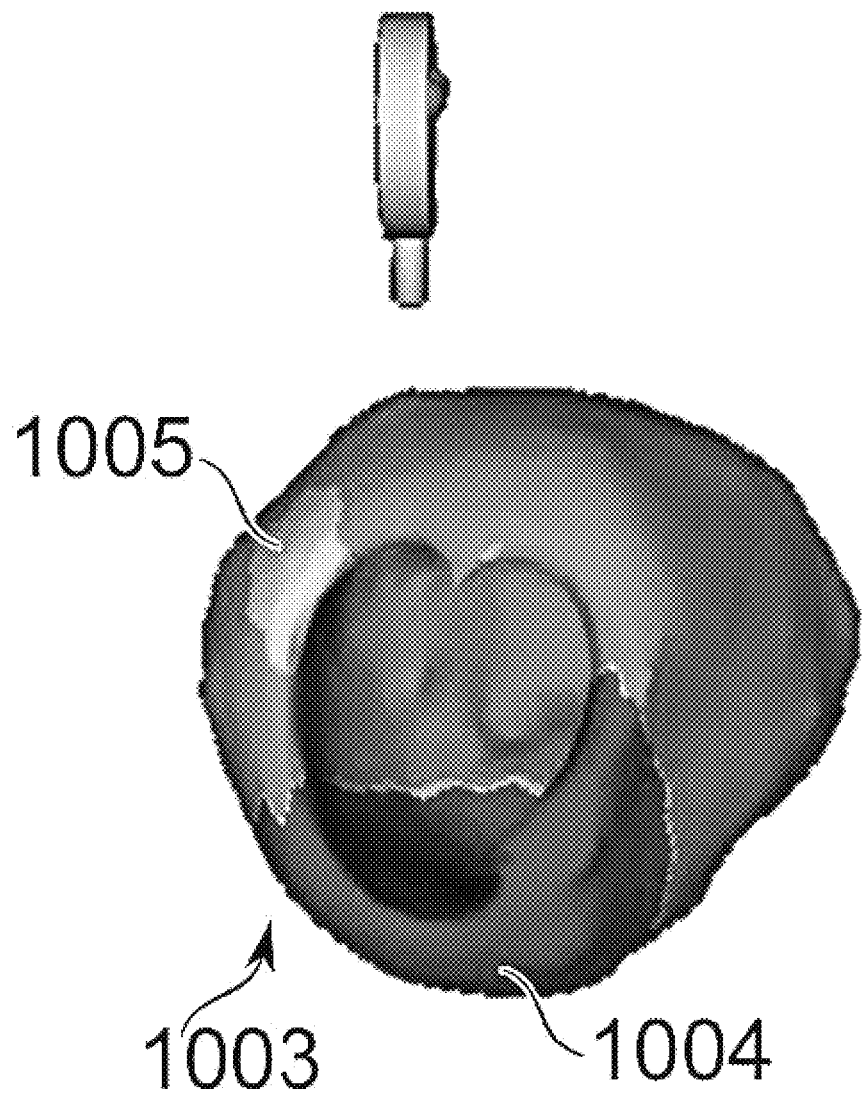
FIG. 10 shows an NM image of left ventricle tissue zones with scarring identified, according to some exemplary embodiments of the invention.
Figure 11:
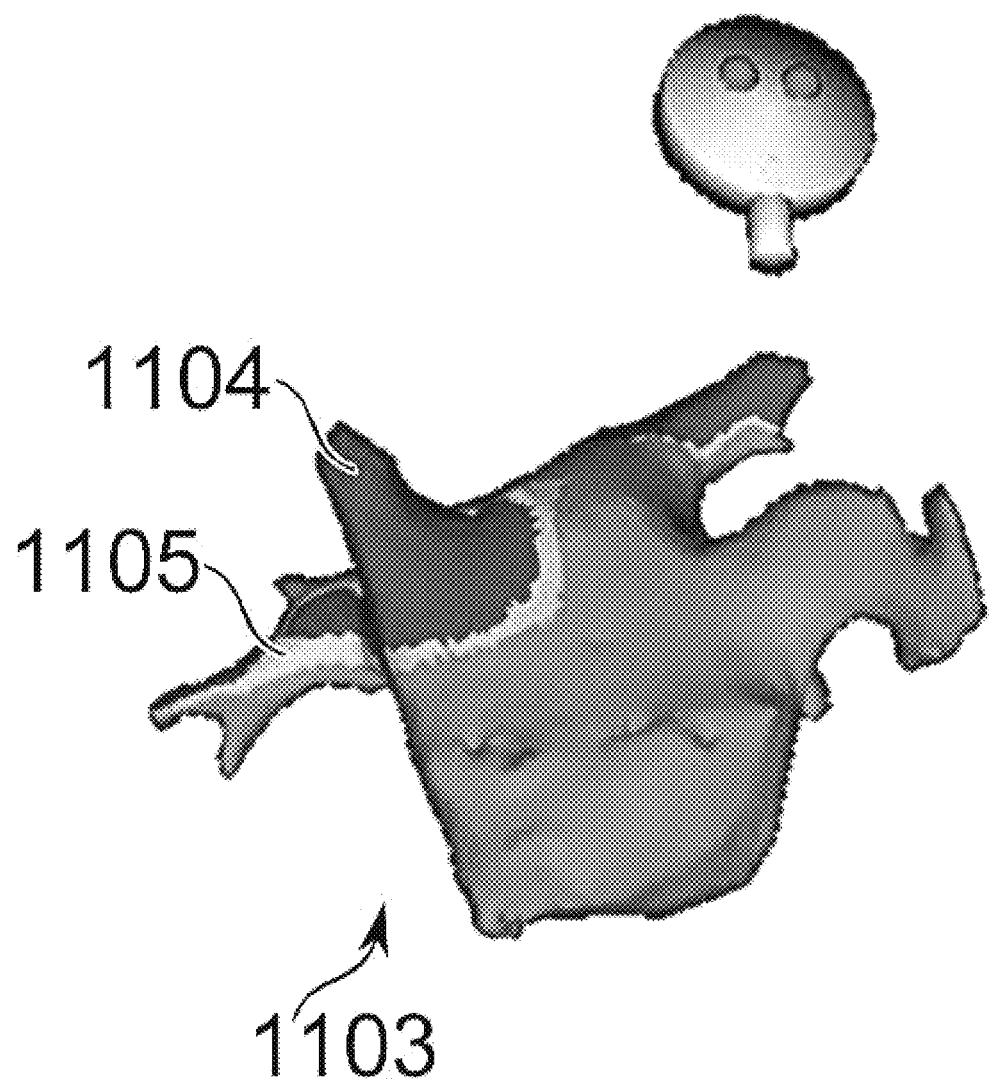
FIGS. 11, 12 and 13 show NM images of left atrium tissue zones with scarring identified, according to some exemplary embodiments of the invention.
Figure 12:
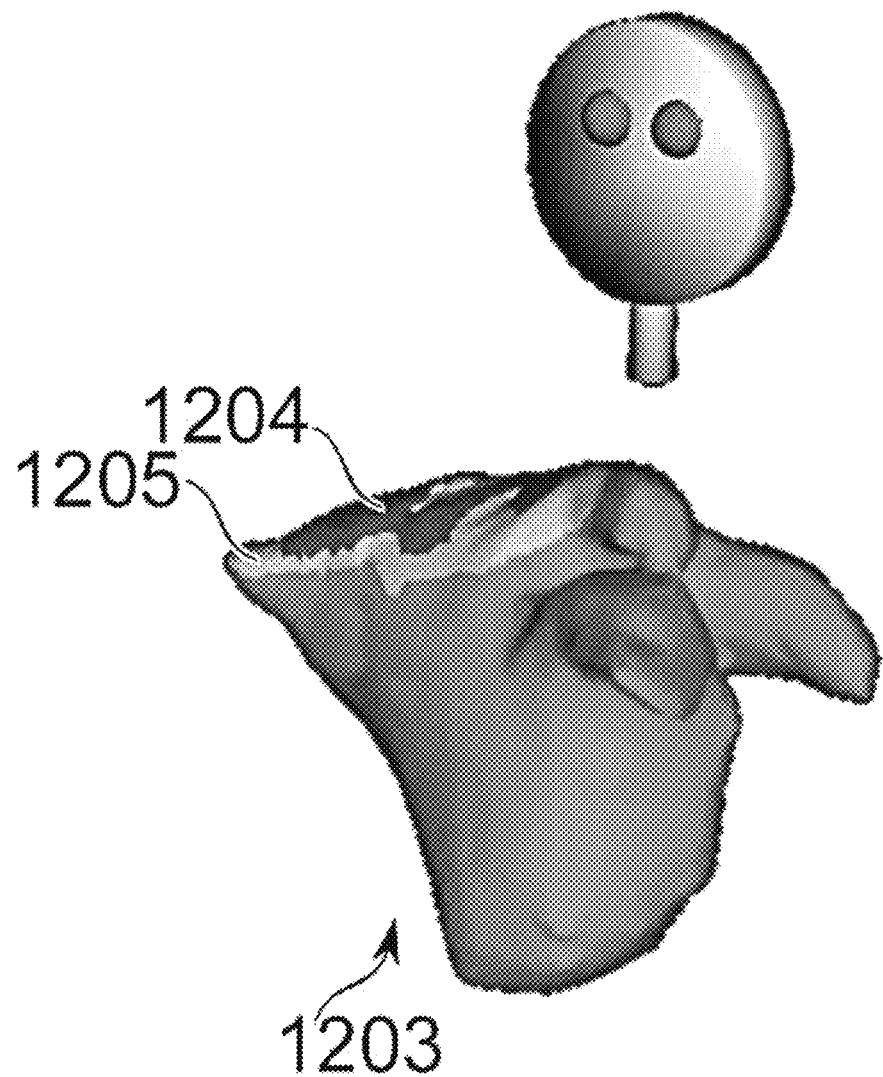
Figure 13:
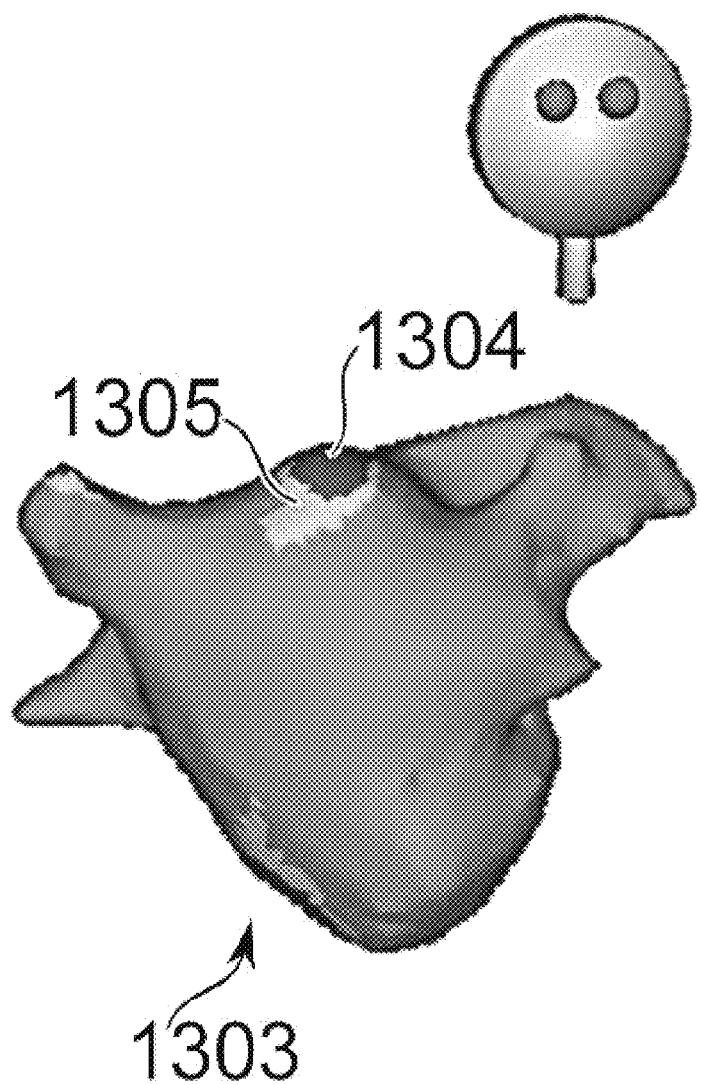

Reference is now made to FIGS. 9 and 11-13, which are nuclear medicine images indicating left atrium tissue zones with scarring, according to some exemplary embodiments of the invention. Reference is also made to FIG. 10, which is a nuclear medicine image indicating left ventricle tissue zones with scarring, according to some exemplary embodiments of the invention.

The left images 903, 1003, 1103, 1203 and 1303 each show a radioimage reconstructed using a MIBI tracer (e.g., Sestamibi) which indicates viability. Red (darker) areas 904, 1004, 1104, 1204 and 1304 indicate complete scarring/fibrosis and yellow areas 905, 1005, 1105, 1205 and 1305 indicate partial fibrosis.

General

It is expected that during the life of a patent maturing from this application many relevant radioimaging techniques will be developed and the scope of the term radioimaging is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of tissue recognition of tissue type in a heart, comprising:
   (i) providing radioactive emission data of cardiac tissue;
   (ii) associating said radioactive emission data with a wall of the heart; and
   (iii) analyzing said radioactive emission data associated with the wall of the heart to recognize fibrous tissue in the heart wall;
   wherein the associating comprises:
      selecting emission locations of the radioactive emission data that correspond with locations of a model of the wall of the heart, and
      reconstructing a nuclear image of radioactive emissions at locations of the heart wall, using values of emission data from the selected emission locations; and
   wherein the analyzing comprises:
      estimating heart wall thickness in the heart wall locations of the nuclear image,
      scaling the values of the emissions of emission data in the nuclear image, using the estimated heart wall thicknesses, to produce a wall-thickness normalized nuclear emission image of the heart wall, and
      categorizing at least one of the heart wall locations as comprising an intermixing of fibrotic tissue and living muscle, based on the wall-thickness normalized nuclear emission image of the heart wall.

2. A method according to claim 1, wherein said analyzing comprises categorizing a shape of a fibrous zone in said heart wall.

3. A method according to claim 1, wherein said analyzing comprises identifying one or more gaps between fibrous zones in said heart wall.

4. A method according to claim 3, wherein said one or more gaps comprises a gap smaller than 5 mm in minimal width.

5. A method according to claim 1, wherein said analyzing comprises identifying one or more fibrous zones with a maximal extent of less than 30 millimeters.

6. A method according to claim 1, wherein said analyzing comprises identifying one or more fibrous zones in an atrial wall.

7. A method according to claim 1, wherein said analyzing comprises identifying one or more fibrous zones that do not reach a full wall thickness.

8. A method according to claim 1, wherein said analyzing comprises identifying one or more fibrous zones that are inside a wall.

9. A method according to claim 1, comprising generating an image of fibrous zones in at least a portion of said heart using the wall-thickness normalized nuclear emission image of the heart wall.

10. A method according to claim 9, wherein said image of fibrous zones has a resolution of better than 5 millimeters.

11. A method according to claim 9, wherein said image of fibrous zones distinguishes between fibrous tissue in different layers of the heart wall.

12. A method according to claim 9, wherein said image of fibrous zones distinguishes between different degrees of fibrosis.

13. A method according to claim 9, wherein said generating comprises normalizing said emission data non-uniformly for different sections of said wall.

14. A method according to claim 9, comprising using said image of fibrous zones for real-time navigation in the body.

15. A method according to claim 1, wherein said analyzing comprises assessing a risk for atrial fibrillation.

16. A method according to claim 1, wherein said analyzing comprises assessing a risk for ventricular arrhythmia.

17. A method according to claim 1, wherein said analyzing comprises planning a correction of an ablation procedure.

18. A method according to claim 1, wherein said associating comprises using a model of said wall.

19. A method according to claim 18, wherein said model is generated from a structural image of said heart.

20. The method of claim 1, wherein the categorizing comprises identifying a location comprising intermixing fibrotic tissue and living muscle occurring throughout an entire thickness of the heart wall location.

21. The method of claim 1, wherein the categorizing comprises estimating, for a plurality of the at least one of the heart wall locations, a corresponding plurality of different graduations of intermixing of fibrotic tissue and living muscle, each graduation indicating a different graduation of fibrosis comprising at least some fibrotic tissue and some living muscle.

22. The method of claim 1, wherein the categorizing comprises distinguishing a plurality of separate layers of the at least one of the heart wall locations, including at least one layer identified as intermixing fibrotic tissue and living muscle.

23. The method of claim 22, wherein the categorizing comprises identifying at least one of the plurality of separate layers located in-between two others of the plurality of separate layers as intermixing fibrotic tissue and living muscle.

24. The method of claim 22, wherein the scaling is performed separately for each of the plurality of separate layers.

25. The method of claim 1, wherein the categorizing comprises identifying a location comprising intermixing fibrotic tissue and living muscle, distinct from a non-transmural scar.

26. The method of claim 1, wherein the model of the heart wall comprises a wall thickness parameter specified with a different value for each of at least 10 locations of the heart wall.

27. A method of tissue recognition of tissue type in a heart, comprising:
 (i) providing radioactive emission data of cardiac tissue;
 (ii) associating said radioactive emission data with respective positions on a wall of the heart;
 (iii) analyzing said radioactive emission data associated with the wall of the heart to recognize fibrous tissue in the heart wall; and
 (iv) producing an image showing fibrotic areas of the heart;
 wherein the associating comprises using a model of said wall generated with thicknesses personalized for the heart.

28. The method of claim 27, wherein the thickness are personalized using a structural image of said heart.

29. The method of claim 27, wherein the model of the heart wall comprises a wall thickness parameter specified with a different value for each of at least 10 locations of the heart wall.

30. A method of tissue recognition of tissue type in a heart, comprising:
 (i) providing radioactive emission data of cardiac tissue;
 (ii) associating said radioactive emission data with respective positions on a wall of the heart;
 (iii) analyzing said radioactive emission data associated with the wall of the heart to recognize fibrous tissue in the heart wall; and
 (iv) producing an image showing fibrotic areas of the heart;
 wherein the analyzing and the image produced differentiate non-transmural scar tissue from fibrosis.

31. The method of claim 27, wherein the differentiating comprises identification of separate layers of the wall of the heart.

* * * * *